United States Patent
Vaccaro et al.

(10) Patent No.: US 9,738,883 B2
(45) Date of Patent: Aug. 22, 2017

(54) PROCESS FOR THE PRODUCTION AND PURIFICATION OF THE COLLAGENASE ENZYME FROM VIBRIO ALGINOLYTICUS

(71) Applicant: FIDIA FARMACEUTICI S.P.A., Abano Terme (IT)

(72) Inventors: Susanna Vaccaro, Abano Terme (IT); Michele Caputo, Abano Terme (IT); Christian Cuppari, Abano Terme (IT); Giovanni Gennari, Abano Terme (IT)

(73) Assignee: FIDIA FARMACEUTICALS S.P.A., Abano Terme (IT)

( * ) Notice: Subject to any disclaimer, the term of this patent is extended or adjusted under 35 U.S.C. 154(b) by 0 days.

(21) Appl. No.: 14/394,481

(22) PCT Filed: Apr. 17, 2013

(86) PCT No.: PCT/EP2013/057998
§ 371 (c)(1),
(2) Date: Oct. 15, 2014

(87) PCT Pub. No.: WO2013/156525
PCT Pub. Date: Oct. 24, 2013

(65) Prior Publication Data
US 2015/0056179 A1 Feb. 26, 2015

(30) Foreign Application Priority Data

Apr. 18, 2012 (IT) .............................. PD2012A0118

(51) Int. Cl.
*C12N 9/52* (2006.01)
*A61K 38/46* (2006.01)
*A61K 38/48* (2006.01)

(52) U.S. Cl.
CPC ............ *C12N 9/52* (2013.01); *A61K 38/4886* (2013.01); *C12Y 304/24003* (2013.01); *C12Y 304/24007* (2013.01)

(58) Field of Classification Search
CPC .................. C12N 9/52; A61K 38/4886; C12Y 304/24003
USPC ........................................ 424/94.67; 435/220
See application file for complete search history.

(56) References Cited

U.S. PATENT DOCUMENTS

| | | | |
|---|---|---|---|
| 4,732,758 A * | 3/1988 | Hurion et al. ............... | 424/94.2 |
| 2007/0224183 A1 * | 9/2007 | Sabatino .................. | C12N 9/52 424/94.63 |

FOREIGN PATENT DOCUMENTS

EP   0 430 635 A1   6/1991

OTHER PUBLICATIONS

Anonymous. Ion Exchange Chromatography Selection Guide; Pall (2015) downloaded from http://www.pall.com/main/laboratory/literature-library-details.p.?id=38542 on Sep. 29, 2015.*
Lecroisey et al., "Purification, Stability and Inhibition of the Collagenase From Achromobacter Iophagus", FEBS Letters, Elsevier, Amsterdam, NL, vol. 59, No. 2, XP002981275, Nov. 1975, pp. 167-172
Takeuchi et al. "Structural gene and complete amino acid sequence of Vibrio alginolyticus collagenase", Biochem. J., vol. 281, XP055047105, 1992, pp. 703-708.
Tong et al., "New Achromobacter collagenase and its immunological relationship with a vertebrate collagenase", Biochimica et Biophysica Acta, Elsevier, NL, vol. 955, No. 1, XP009165583, Nov. 19, 1987, pp. 43-49.
Tong et al., "Purification and characterization of two high-molecular-mass forms of Achromobacter collagenase", Biochimica et Biophysica Acta, Elsevier, Amsterdam, NL, vol. 874, No. 3, XP025210494, Dec. 12, 1986, pp. 296-304.

* cited by examiner

*Primary Examiner* — Scott Long
*Assistant Examiner* — Paul Martin
(74) *Attorney, Agent, or Firm* — Birch, Stewart, Kolasch & Birch, LLP

(57) ABSTRACT

The present invention claims a novel process for the production and purification of microbial collagenase (Microbial Collagenase EC 3.4.24.3) produced by the non-pathogenic aerobic bacterium *Vibrio alginolyticus* chemovar. *iophagus* (NCIMB Number: 1 1038, synonym LMG 3418, hereinafter called *Vibrio alginolyticus*), which said process provides high production levels of collagenase with a stable, reproducible, cheap fermentation process. The collagenase produced from *Vibrio alginolyticus* according to the process described herein also presents a specific activity superior to that of other microbial collagenases, is stable in aqueous solution, and can be frozen without significant damage. A further subject of the present invention is pharmaceutical compositions containing collagenase obtained according to the production and purification process described, for the purpose of therapeutic treatment of disorders characterized by collagen accumulation or for the treatment of blemishes/imperfections that benefit from reducing local collagen accumulations.

3 Claims, 12 Drawing Sheets

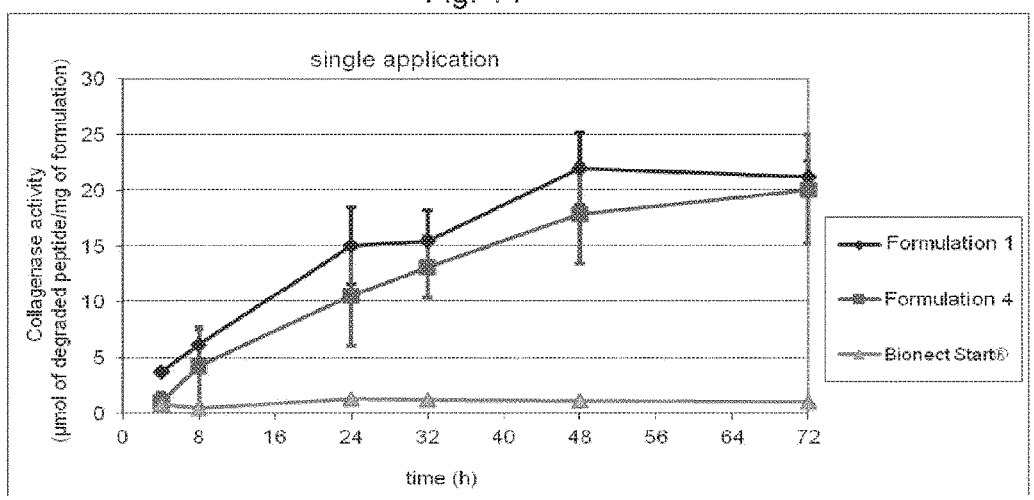

SEQUENCE LISTING

```
<160> NUMBER OF SEQ ID NOS: 3

<210> SEQ ID NO 1
<211> LENGTH: 739
<212> TYPE: PRT
<213> ORGANISM: Vibrio alginolyticus
<220> FEATURE:
<221> NAME/KEY: mat_peptide
<222> LOCATION: (1)..(739)
<223> OTHER INFORMATION: Active core of collagenase from Vibrio
      alginolyticus

<400> SEQUENCE: 1

Thr Ala Cys Asp Leu Glu Ala Leu Val Thr Glu Ser Ser Asn Gln Leu
1               5                   10                  15

Ile Ser Glu Ile Leu Ser Gln Gly Ala Thr Cys Val Asn Gln Leu Phe
            20                  25                  30

Ser Ala Glu Ser Arg Ile Gln Glu Ser Val Phe Ser Ser Asp His Met
        35                  40                  45

Tyr Asn Ile Ala Lys His Thr Thr Leu Ala Lys Gly Tyr Thr Gly
    50                  55                  60

Gly Gly Ser Asp Glu Leu Glu Thr Leu Phe Leu Tyr Leu Arg Ala Gly
65                  70                  75                  80

Tyr Tyr Ala Glu Phe Tyr Asn Asp Asn Ile Ser Phe Ile Glu Trp Val
                85                  90                  95

Thr Pro Ala Val Lys Glu Ser Val Asp Ala Phe Val Asn Thr Ala Ser
            100                 105                 110
```

```
Phe Tyr Glu Asn Ser Asp Arg His Gly Lys Val Leu Ser Glu Val Ile
            115                 120                 125

Ile Thr Met Asp Ser Ala Gly Leu Gln His Ala Tyr Leu Pro Gln Val
        130                 135                 140

Thr Gln Trp Leu Thr Arg Trp Asn Asp Gln Tyr Ala Gln His Trp Tyr
145                 150                 155                 160

Met Arg Asn Ala Val Asn Gly Val Phe Thr Ile Leu Phe Gly Gly Gln
                165                 170                 175

Trp Asn Glu Gln Phe Val Gln Ile Ile Gly Asn Gln Thr Asp Leu Ala
            180                 185                 190

Lys Ala Leu Gly Asp Phe Ala Leu Arg Ala Ser Ser Ile Gly Ala Glu
        195                 200                 205

Asp Glu Phe Met Ala Ala Asn Ala Gly Arg Glu Leu Gly Arg Leu Thr
210                 215                 220

Lys Tyr Thr Gly Asn Ala Ser Ser Val Val Lys Ser Gln Leu Ser Arg
225                 230                 235                 240

Ile Phe Glu Gln Tyr Glu Met Tyr Gly Arg Gly Asp Ala Val Trp Leu
                245                 250                 255

Ala Ala Ala Asp Thr Ala Ser Tyr Tyr Ala Asp Cys Ser Glu Phe Gly
            260                 265                 270

Ile Cys Asn Phe Glu Thr Glu Leu Lys Gly Leu Val Leu Ser Gln Thr
        275                 280                 285

Tyr Thr Cys Ser Pro Thr Ile Arg Ile Leu Ser Gln Asn Met Thr Gln
290                 295                 300

Glu Gln His Ala Ala Cys Ser Lys Met Gly Tyr Glu Gly Tyr
305                 310                 315                 320

Phe His Gln Ser Leu Glu Thr Gly Glu Gln Pro Val Lys Asp Asp His
                325                 330                 335

Asn Thr Gln Leu Gln Val Asn Ile Phe Asp Ser Ser Thr Asp Tyr Gly
            340                 345                 350

Lys Tyr Ala Gly Pro Ile Phe Asp Ile Ser Thr Asp Asn Gly Gly Met
        355                 360                 365

Tyr Leu Glu Gly Asp Pro Ser Gln Pro Gly Asn Ile Pro Asn Phe Ile
370                 375                 380

Ala Tyr Glu Ala Ser Tyr Ala Asn Ala Asp His Phe Val Trp Asn Leu
385                 390                 395                 400

Glu His Glu Tyr Val His Tyr Leu Asp Gly Arg Phe Asp Leu Tyr Gly
                405                 410                 415

Gly Phe Ser His Pro Thr Glu Lys Ile Val Trp Trp Ser Glu Gly Ile
            420                 425                 430

Ala Glu Tyr Val Ala Gln Glu Asn Asp Asn Gln Ala Ala Leu Glu Thr
        435                 440                 445

Ile Leu Asp Gly Ser Thr Tyr Thr Leu Ser Glu Ile Phe Glu Thr Thr
450                 455                 460

Tyr Asp Gly Phe Asp Val Asp Arg Ile Tyr Arg Trp Gly Tyr Leu Ala
465                 470                 475                 480

Val Arg Phe Met Phe Glu Asn His Lys Asp Asp Val Asn Gln Met Leu
                485                 490                 495

Val Glu Thr Arg Gln Gly Asn Trp Ile Asn Tyr Lys Ala Thr Ile Thr
            500                 505                 510

Gln Trp Ala Asn Leu Tyr Gln Ser Glu Phe Glu Gln Trp Gln Gln Thr
        515                 520                 525
```

-continued

```
Leu Val Ser Asn Gly Ala Pro Asn Ala Val Ile Thr Ala Asn Ser Lys
        530                 535                 540

Gly Lys Val Gly Glu Ser Ile Thr Phe Ser Ser Glu Asn Ser Thr Asp
545                 550                 555                 560

Pro Asn Gly Lys Ile Val Ser Val Leu Trp Asp Phe Gly Asp Gly Ser
                565                 570                 575

Thr Ser Thr Gln Thr Lys Pro Thr His Gln Tyr Gly Ser Glu Gly Glu
            580                 585                 590

Tyr Ser Val Ser Leu Ser Val Thr Asp Ser Glu Gly Leu Thr Ala Thr
        595                 600                 605

Ala Thr His Thr Val Val Ile Ser Ala Leu Gly Gly Asn Asp Thr Leu
    610                 615                 620

Pro Gln Asp Cys Ala Val Gln Ser Lys Val Ser Gly Gly Arg Leu Thr
625                 630                 635                 640

Ala Gly Glu Pro Val Cys Leu Ala Asn Gln Gln Thr Ile Trp Leu Ser
                645                 650                 655

Val Pro Ala Val Asn Glu Ser Ser Asn Leu Ala Ile Thr Thr Gly Asn
            660                 665                 670

Gly Thr Gly Asn Leu Lys Leu Glu Tyr Ser Asn Ser Gly Trp Pro Asp
        675                 680                 685

Asp Thr Asn Leu His Gly Trp Ser Asp Asn Ile Gly Asn Gly Glu Cys
    690                 695                 700

Ile Thr Leu Ser Asn Gln Ser Asn Tyr Trp Gly Tyr Val Lys Val Ser
705                 710                 715                 720

Gly Asp Phe Glu Asn Ala Ala Ile Val Val Asp Phe Asp Ala Gln Lys
                725                 730                 735

Cys Arg Gln

<210> SEQ ID NO 2
<211> LENGTH: 814
<212> TYPE: PRT
<213> ORGANISM: Vibrio alginolyticus
<220> FEATURE:
<221> NAME/KEY: PEPTIDE
<222> LOCATION: (1)..(814)
<223> OTHER INFORMATION: Microbial collagenase EC 3.4.24.3 from Vibrio
      Alginolyticus

<400> SEQUENCE: 2

Met Glu Leu Lys Ile Leu Ser Val Ala Ile Ala Thr Thr Leu Thr Ser
1               5                   10                  15

Thr Gly Val Phe Ala Leu Ser Glu Pro Val Ser Gln Val Thr Glu Gln
            20                  25                  30

His Ala His Ser Ala His Thr His Gly Val Glu Phe Asn Arg Val Glu
        35                  40                  45

Tyr Gln Pro Thr Ala Thr Leu Pro Ile Gln Pro Ser Lys Ala Thr Arg
    50                  55                  60

Val Gln Ser Leu Glu Ser Leu Asp Glu Ser Ser Thr Ala Cys Asp Leu
65                  70                  75                  80

Glu Ala Leu Val Thr Glu Ser Ser Asn Gln Leu Ile Ser Glu Ile Leu
                85                  90                  95

Ser Gln Gly Ala Thr Cys Val Asn Gln Leu Phe Ser Ala Glu Ser Arg
            100                 105                 110

Ile Gln Glu Ser Val Phe Ser Ser Asp His Met Tyr Asn Ile Ala Lys
        115                 120                 125
```

-continued

```
His Thr Thr Thr Leu Ala Lys Gly Tyr Thr Gly Gly Gly Ser Asp Glu
    130                 135                 140

Leu Glu Thr Leu Phe Leu Tyr Leu Arg Ala Gly Tyr Tyr Ala Glu Phe
145                 150                 155                 160

Tyr Asn Asp Asn Ile Ser Phe Ile Glu Trp Val Thr Pro Ala Val Lys
                165                 170                 175

Glu Ser Val Asp Ala Phe Val Asn Thr Ala Ser Phe Tyr Glu Asn Ser
            180                 185                 190

Asp Arg His Gly Lys Val Leu Ser Glu Val Ile Ile Thr Met Asp Ser
        195                 200                 205

Ala Gly Leu Gln His Ala Tyr Leu Pro Gln Val Thr Gln Trp Leu Thr
    210                 215                 220

Arg Trp Asn Asp Gln Tyr Ala Gln His Trp Tyr Met Arg Asn Ala Val
225                 230                 235                 240

Asn Gly Val Phe Thr Ile Leu Phe Gly Gly Gln Trp Asn Glu Gln Phe
                245                 250                 255

Val Gln Ile Ile Gly Asn Gln Thr Asp Leu Ala Lys Ala Leu Gly Asp
            260                 265                 270

Phe Ala Leu Arg Ala Ser Ser Ile Gly Ala Glu Asp Glu Phe Met Ala
    275                 280                 285

Ala Asn Ala Gly Arg Glu Leu Gly Arg Leu Thr Lys Tyr Thr Gly Asn
290                 295                 300

Ala Ser Ser Val Val Lys Ser Gln Leu Ser Arg Ile Phe Glu Gln Tyr
305                 310                 315                 320

Glu Met Tyr Gly Arg Gly Asp Ala Val Trp Leu Ala Ala Ala Asp Thr
                325                 330                 335

Ala Ser Tyr Tyr Ala Asp Cys Ser Glu Phe Gly Ile Cys Asn Phe Glu
            340                 345                 350

Thr Glu Leu Lys Gly Leu Val Leu Ser Gln Thr Tyr Thr Cys Ser Pro
        355                 360                 365

Thr Ile Arg Ile Leu Ser Gln Asn Met Thr Gln Glu Gln His Ala Ala
    370                 375                 380

Ala Cys Ser Lys Met Gly Tyr Glu Glu Gly Tyr Phe His Gln Ser Leu
385                 390                 395                 400

Glu Thr Gly Glu Gln Pro Val Lys Asp Asp His Asn Thr Gln Leu Gln
                405                 410                 415

Val Asn Ile Phe Asp Ser Ser Thr Asp Tyr Gly Lys Tyr Ala Gly Pro
            420                 425                 430

Ile Phe Asp Ile Ser Thr Asp Asn Gly Gly Met Tyr Leu Glu Gly Asp
        435                 440                 445

Pro Ser Gln Pro Gly Asn Ile Pro Asn Phe Ile Ala Tyr Glu Ala Ser
    450                 455                 460

Tyr Ala Asn Ala Asp His Phe Val Trp Asn Leu Glu His Glu Tyr Val
465                 470                 475                 480

His Tyr Leu Asp Gly Arg Phe Asp Leu Tyr Gly Gly Phe Ser His Pro
                485                 490                 495

Thr Glu Lys Ile Val Trp Trp Ser Glu Gly Ile Ala Gly Tyr Val Ala
            500                 505                 510

Gln Glu Asn Asp Asn Gln Ala Ala Leu Glu Thr Ile Leu Asp Gly Ser
        515                 520                 525

Thr Tyr Thr Leu Ser Glu Ile Phe Glu Thr Thr Tyr Asp Gly Phe Asp
    530                 535                 540
```

```
Val Asp Arg Ile Tyr Arg Trp Gly Tyr Leu Ala Val Arg Phe Met Phe
545                 550                 555                 560

Glu Asn His Lys Asp Asp Val Asn Gln Met Leu Val Glu Thr Arg Gln
                565                 570                 575

Gly Asn Trp Ile Asn Tyr Lys Ala Thr Ile Thr Gln Trp Ala Asn Leu
            580                 585                 590

Tyr Gln Ser Glu Phe Glu Gln Trp Gln Gln Thr Leu Val Ser Asn Gly
        595                 600                 605

Ala Pro Asn Ala Val Ile Thr Ala Asn Ser Lys Gly Lys Val Gly Glu
        610                 615                 620

Ser Ile Thr Phe Ser Ser Glu Asn Ser Thr Asp Pro Asn Gly Lys Ile
625                 630                 635                 640

Val Ser Val Leu Trp Asp Phe Gly Asp Gly Ser Thr Ser Thr Gln Thr
                645                 650                 655

Lys Pro Thr His Gln Tyr Gly Ser Glu Gly Glu Tyr Ser Val Ser Leu
                660                 665                 670

Ser Val Thr Asp Ser Glu Gly Leu Thr Ala Thr Ala Thr His Thr Val
            675                 680                 685

Val Ile Ser Ala Leu Gly Gly Asn Asp Thr Leu Pro Gln Asp Cys Ala
        690                 695                 700

Val Gln Ser Lys Val Ser Gly Gly Arg Leu Thr Ala Gly Glu Pro Val
705                 710                 715                 720

Cys Leu Ala Asn Gln Gln Thr Ile Trp Leu Ser Val Pro Ala Val Asn
                725                 730                 735

Glu Ser Ser Asn Leu Ala Ile Thr Thr Gly Asn Gly Thr Gly Asn Leu
            740                 745                 750

Lys Leu Glu Tyr Ser Asn Ser Gly Trp Pro Asp Asp Thr Asn Leu His
            755                 760                 765

Gly Trp Ser Asp Asn Ile Gly Asn Gly Glu Cys Ile Thr Leu Ser Asn
770                 775                 780

Gln Ser Asn Tyr Trp Gly Tyr Val Lys Val Ser Gly Asp Phe Glu Asn
785                 790                 795                 800

Ala Ala Ile Val Val Asp Phe Asp Ala Gln Lys Cys Arg Gln
                805                 810

<210> SEQ ID NO 3
<211> LENGTH: 15
<212> TYPE: PRT
<213> ORGANISM: Vibrio Alginolyticus
<220> FEATURE:
<221> NAME/KEY: MISC_FEATURE
<222> LOCATION: (1)..(15)
<223> OTHER INFORMATION: N terminal of the mature chain

<400> SEQUENCE: 3

Thr Ala Cys Asp Leu Glu Ala Leu Val Thr Glu Ser Ser Asn Gln
1               5                   10                  15
```

PROCESS FOR THE PRODUCTION AND PURIFICATION OF THE COLLAGENASE ENZYME FROM VIBRIO ALGINOLYTICUS

CROSS REFERENCE TO RELATED APPLICATIONS

This application is the National Phase of PCT International Application No. PCT/EP2013/057998, filed on Apr. 17, 2013, which claims priority under 35 U.S.C. 119(a) to Patent Application No. PD2012A000118, filed in Italy on Apr. 18, 2012, all of which are hereby expressly incorporated by reference into the present application.

FIELD OF INVENTION

Collagenases are metalloenzymes with a proteolytic activity which require the zinc ion in the active site in order to perform their specific function of breaking down native collagen. Unlike other proteases, they can hydrolyse collagen under physiological pH and temperature conditions. A number of collagenases produced by bacteria are known in the prior art (*Vibrio, Clostridium, Streptomyces, Pseudomonas*); those produced by *Clostridium* (Santyl®, Noruxol®) are widely used in pharmaceutical compositions for the treatment of skin ulcers of various origins, bedsores, burns of different degrees and hypertrophic scars, because they break down the collagen present in the necrotic tissue. This facilitates the removal of cell debris, which often constitutes an obstacle to the migration of epithelial cells during the wound-healing and re-epithelialisation process (Rao, D. B. et al., 1975). Collagenase from *Vibrio* was also used recently for similar purposes (EP1901755); this patent describes solely lipophilic compositions (lipogels) containing carrageenan as stabilising agent. However, the inflammatory role generally played by that substance is known to the skilled person. In any event, regardless of its origin, collagenase has extremely low stability in an aqueous carrier, and is therefore always formulated in wholly lipophilic carriers; Santyl®, Noruxol® and Bionect Start® are ointments with a wholly lipophilic base in which the enzyme is never distributed evenly, and is subject to a significant loss of activity over time.

The lipophilic carrier ensures the stability of the enzyme and the storability of the pharmaceutical product, while penalising its therapeutic activity; collagenase is released from the lipophilic carrier very slowly, with the result that its bioavailability is greatly limited. Collagenase can also be used for the systemic treatment, in particular by injection, of disorders such as adhesive capsulitis (frozen shoulder), Dupuytren's contracture, Peyronie's disease, cellulitis and post-surgical adhesions. Stability in the aqueous carrier is crucial for these applications. A product for injective treatment of Dupuytren's contracture is currently on the market (a lyophilic substance reconstituted at the time of use) which contains a mixture of two collagenases in a precise weight ratio, which are extracted and purified by fermentation of the bacterium *Clostridium histolyticum*.

As already stated, the latter is one of the most common sources of collagenase; however, it is a pathogenic micro-organism, which needs anaerobic fermentation (Mandl, I. et al., 1958, *Arch Biochem Biophys*, 74:465-475).

The collagenolytic activity of some strains of *Achromobacter* was identified for the first time in 1972 (Thomson, J. A., Woods, D. R. and Welton, R. L. 1972), and the first studies were subsequently conducted on the strain *Achromobacter iophagus* (subsequently reclassified as *Vibrio alginolyticus* chemovar. *iophagus*, Emod, I. et al. 1983) which demonstrated the presence of a collagenase with high specific activity (Welton and Woods 1973). As regards the choice of micro-organism to be used to produce collagenase by fermentation, the use of *Vibrio alginolyticus* is much more advantageous than *Clostridium histolyticum*, because it is non-pathogenic and allows the fermentation to be performed in an aerobic environment, with considerable industrial advantages. The pathogenicity of the microbial strain is an important aspect, because any impurities (microbial or protein residues) in the finished product can give rise to serious side effects. Working with pathogenic strains obviously requires particular care at the purification stages, and consequently a more complex, expensive industrial process.

The microbial collagenase EC 3.4.24.3 produced from *Vibrio alginolyticus* is a $Zn^{2+}$ metalloprotease which is also distinguished from the collagenases produced by *Clostridium histolyticum* for a number of reasons:

it acts specifically on the synthetic peptide Pz-Pro-Leu-Gly-Ala-D-Arg (where PZ=4-phenyl azobenzyl oxycarbonyl), which is the synthetic substrate of choice for the evaluation of collagenolytic activity. The collagenase from *V. alginolyticus* produced according to the present invention is the only one able to break down collagen at the Leu-Gly bond (Keil, B., Gilles A.-M., Lecroisey, A., Hurion, N. and Tong, N.-T. 1975; Keil B. Matrix Suppl. 1992; 1:127-33);

it has much greater proteolytic activity than the analogue obtained from *Clostridium histolyticum;* it has a specificity at the cleavage site on native collagen; it cleaves the helical chain of native collagen at 2 sites, preferably at ¾ from the N-terminal end at the Y-Gly bond of the Pro-Y-Gly-Pro sequence, where Y is a neutral amino acid. Conversely, collagenase from *Clostridium histolyticum* presents various cleavage sites in the native collagen chain (Lecroisey, A. Keil, B. 1979);

The *Vibrio alginolyticus* chemovar. *Iophagus* strain only produces one collagenase, although SDS-PAGE analysis of the products of purification demonstrates the presence of several bands with different molecular weights where collagenolytic activity is maintained. These low molecular weight species have been attributed to a process of auto-proteolysis of the enzyme which is inhibited by specifically formulated buffers (Keil-Dlouha, V. 1976).

In 1992, Takeuchi et al. cloned the entire sequence encoding for collagenase from *Vibrio alginolyticus*. The amino-acid sequence deduced from the nucleotide sequence shows that mature collagenase is formed by 739 amino acids with a molecular weight of 81,875 Da. The nucleotide and amino-acid sequences of collagenase from *Vibrio alginolyticus* do not exhibit any significant similarities with those of other collagenases (Takeuchi, H., 1992). To date, processes for the production of the enzyme from the strain in question have produced rather modest yields and products with an unsatisfactory degree of purity, especially for injectable use. Patent EP 0115974 describes a process for the production and purification of collagenase from *V. alginolyticus*; the final product is a mixture of enzymes (collagenase, neutral proteases and endonuclease) which is only stable after the addition of bovine skin collagen fragments (ASF).

The material obtained has a very low degree of purity. Moreover, the presence of ASF can create problems at the time of preparation of the pharmaceutical forms identified or, in particular, as it is a material of animal origin, when the chosen pharmaceutical compositions are administered by injection.

Moreover, as already stated, the pharmaceutical compositions currently known take the form of an ointment, whereas for topical applications and, above all, for systemic applications, it is essential for the collagenase enzyme to be in extremely pure form and stable in an aqueous carrier (to improve the distribution of the enzyme in the composition); an aqueous carrier is absolutely preferred for injection treatment.

The present invention overcomes these problems by disclosing an innovative process for the production and purification of the enzyme collagenase from *V. alginolyticus*, a process characterised by high yields, reproducibility, stability and a high degree of purity of the finished product. The finished product is also stable in aqueous solution and can therefore be stored for long periods, even at temperatures ranging between −20 and −80° C., without undergoing significant damage.

Due to the high degree of purity and the specificity of cleavage on the collagen chain, the collagenase claimed herein can also be used to dissociate tissues and isolate cell clusters or single cells for all experimental and therapeutic procedures requiring isolated cells.

Figure 11:
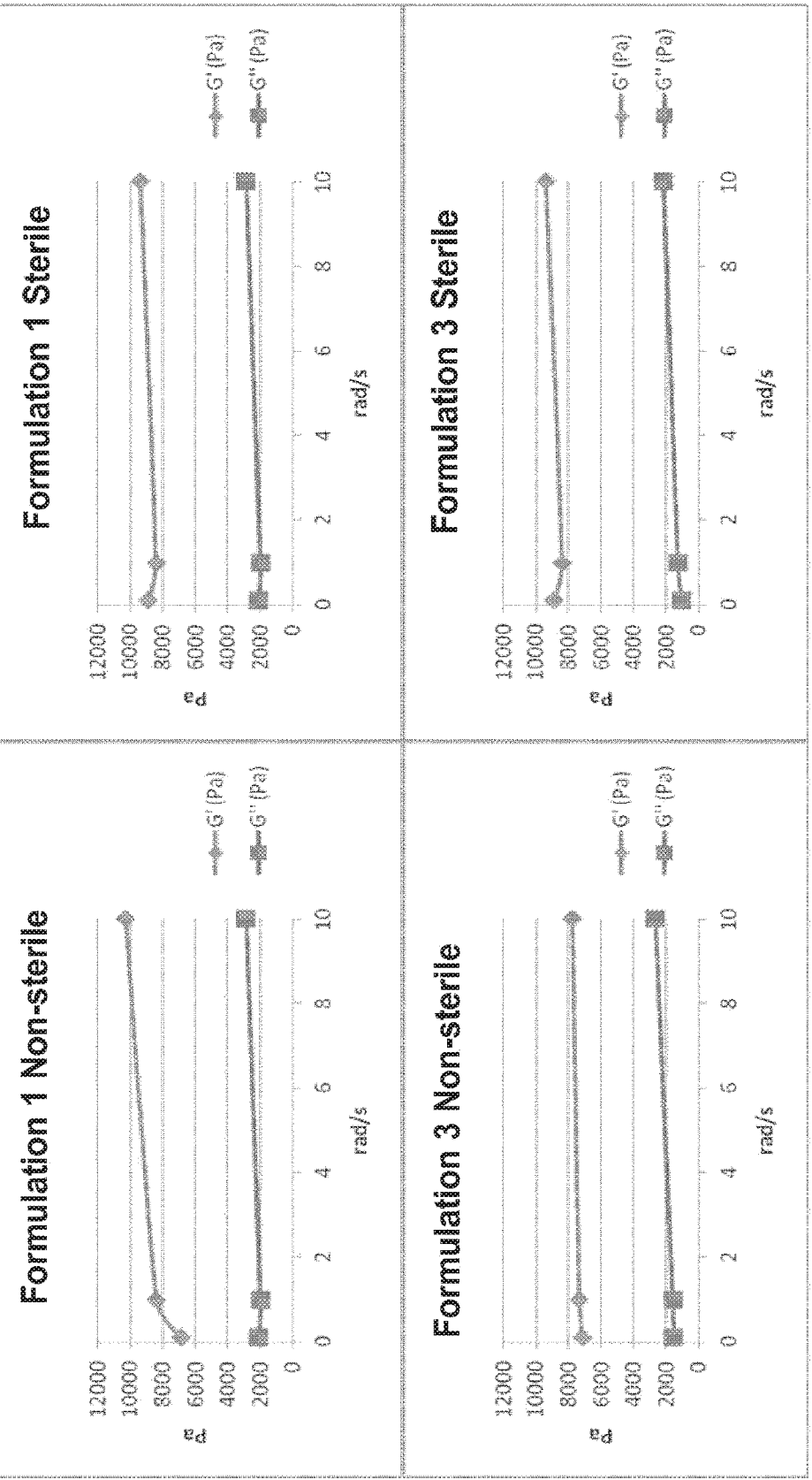

FIG. 11 provides four graphs showing the pre- and post-sterilization rheological evaluation of the present invention.

Figure 12:
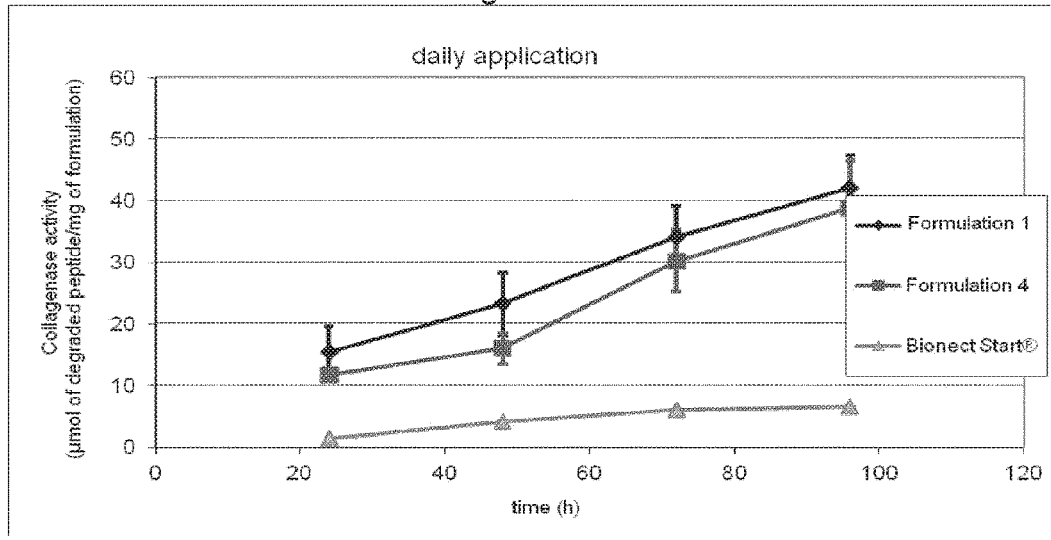

FIG. 12 provides a graph showing the collagenase activity of different formulations over time for daily application.

Figure 13:
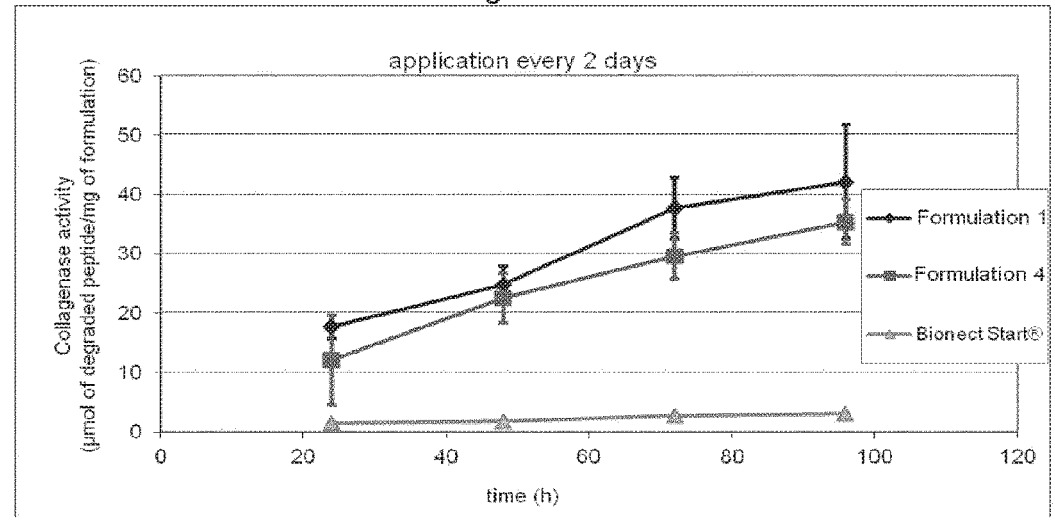

FIG. 13 provides a graph showing the collagenase activity of different formulations over time for application every two days.

FIG. 14 provides a graph showing the collagenase activity of different formulations over time for daily application.

DETAILED DESCRIPTION OF THE INVENTION

The present invention claims a novel process for the production and purification of microbial collagenase (Microbial Collagenase EC 3.4.24.3) produced by the non-pathogenic aerobic bacterium *Vibrio alginolyticus* chemovar. *iophagus* (NCIMB Number: 11038, synonym LMG 3418, hereinafter called *Vibrio alginolyticus*); said process provides high production levels of collagenase with a stable, reproducible, cheap fermentation process. The sequence of collagenase produced from *Vibrio alginolyticus* according to the production and purification process herein described (SEQ ID NO: 1) is characterized by the deletion of the amino acids 1-75 in comparison with the sequence of 814 amino acids encoded by the gene of the collagenase from *V. alginolyticus* (herein reported as SEQ ID NO: 2 corresponding to Microbial collagenase EC 3.4.24.3). By the process of the invention, the mature protein, that is the active core, consisting of 739 aa, more precisely the 76-814 aa, is produced:

```
                                          (SEQ ID NO: 1)
TACDLEALVTESSNQLISEILSQGATCVNQLFSAESRIQESVFSSDHMYN

IAKHTTTLAKGYTGGGSDELETLFLYLRAGYYAEFYNDNISFIEWVTPAV

KESVDAFVNTASFYENSDRHGKVLSEVIITMDSAGLQHAYLPQVTQWLTR

WNDQYAQHWYMRNAVNGVFTILFGGQWNEQFVQIIGNQTDLAKALGDFAL

RASSIGAEDEFMAANAGRELGRLTKYTGNASSVVKSQLSRIFEQYEMYGR

GDAVWLAAADTASYYADCSEFGICNFETELKGLVLSQTYTCSPTIRILSQ

NMTQEQHAAACSKMGYEEGYFHQSLETGEQPVKDDHNTQLQVNIFDSSTD

YGKYAGPIFDISTDNGGMYLEGDPSQPGNIPNFIAYEASYANADHFVWNL

EHEYVHYLDGRFDLYGGFSHPTEKIVWWSEGIAEYVAQENDNQAALETIL

DGSTYTLSEIFETTYDGFDVDRIYRWGYLAVRFMFENHKDDVNQMLVETR

QGNWINYKATITQWANLYQSEFEQWQQTLVSNGAPNAVITANSKGKVGES

ITFSSENSTDPNGKIVSVLWDFGDGSTSTQTKPTHQYGSEGEYSVSLSVT

DSEGLTATATHTVVISALGGNDTLPQDCAVQSKVSGGRLTAGEPVCLANQ

QTIWLSVPAVNESSNLAITTGNGTGNLKLEYSNSGWPDDTNLHGWSDNIG

NGECITLSNQSNYWGYVKVSGDFENAAIVVDFDAQKCRQ
```

Furthermore the collagenase produced from *Vibrio alginolyticus* according to the process of the invention also presents a specific activity superior to that of other microbial collagenases, is purer and stable in aqueous solution, and can be frozen without significant damage.

Therefore a further object of the present invention is the collagenase, obtained according the described production and purification process, for the use in the therapeutic treatment of pathologies characterized by the accumulation of collagen or in the treatment of blemishes/imperfections that benefit from reducing local collagen accumulations; such as for example, it is worth to mention, skin ulcers of various origins, bedsores, burns of different degrees, scalds, and hypertrophic scars, cellulitis, post-surgical adhesions and still "frozen shoulder" or adhesive capsulitis, Dupuytren's contracture, Peyronie's disease.

A further object of the present invention is pharmaceutical compositions containing collagenase obtained according to the described production and purification process, for the use in the therapeutic treatment of disorders characterised by collagen accumulation or for the treatment of blemishes/imperfections that benefit from reducing local collagen accumulations; examples are skin ulcers of various origins, bedsores, burns of different degrees, scalds, and hypertrophic scars, cellulitis, post-surgical adhesions, adhesive capsulitis (frozen shoulder), Dupuytren's contracture and Peyronie's disease.

The collagenase obtained as described herein is also suitable for application in tissue dissociation and isolation of cell clusters or single cells. This application is used, for example, in the Langerhans islet cell transplantation procedure to isolate the islet cells from the surrounding pancreatic tissue, and in general in all experimental and therapeutic procedures requiring tissue dissociation.

The collagenase obtained by the process described below is characterised by:
- molecular weight 82 Kda;
- specific activity between 1000 and 1800 nkat/mg;
- purity between 98.0 and 100%;
- absence of microbial and protein contaminants, specifically absence of endotoxins and DNA;
- stability at a pH of between 5.5 and 11;
- stability in aqueous solution at a T ranging between 4° and 40° C., particularly stable at 37° C.;
- stability in aqueous solution at 4° C. for 30 days;
- stability in aqueous solution at a T ranging between −20° C. and −80° C. for 24-48 months;
- lyophilisability to obtain a stable freeze-dried powder.

It is preferably also characterised by
- N-terminal sequence: H$_2$N-Thr-Ala-Cys-Asp-Leu-Glu-Ala-Leu-Val-Thr-Glu-Ser-Ser-Asn-Gln (SEQ ID NO:3);
- inhibition by Ag and Cu salts and the chelating agent EDTA;
- storability at temperatures ranging between −20 and −80° C., i.e. in frozen form, without significant loss of enzyme activity (5-15%).

The collagenase production and purification process according to the invention comprises the following stages:

Stage A: Inoculation of *Vibrio alginolyticus* chemovar. *iophagus* into an Erlenmeyer flask and fermentation with culture broth of non-bovine animal origin;

Stage B: Clarification of the fermented broth thus obtained by tangential flow ultrafiltration (TFF1) with 100-500 kD Molecular Weight Cut-Off (MWCO) cassettes, preferably 300 kD;

Stage C: Dialysis and concentration of the clarified medium obtained in stage B, by tangential flow ultrafiltration (TFF2) with 5-30 kD MWCO cassettes, preferably 10 kD MWCO;

Stage D: Purification of the solution containing collagenase obtained in Stage C, by anion-exchange resin carrying weak basic groups, at a pH of between 6.9 and 7.4, preferably at a pH of 7.1;

Stage E: Dialysis and concentration of the fractions collected which have collagenolytic activity, originating from Stage D, by tangential flow ultrafiltration (TFF3) with 10-50 kD MWCO cassettes, preferably 30 kD MWCO;

Stage F: Purification of the solution thus obtained, by anion-exchange resin carrying strong basic groups, at a pH of between 6.9 and 7.4, preferably at a pH of 7.1;

Stage G: Diafiltration and concentration of the fractions with collagenolytic activity ≥95% originating from stage F, by tangential flow ultrafiltration (TFF4) with 10-50 kD MWCO cassettes, preferably 30 kD MWCO;

Stage H: Filtration of the solution containing collagenase thus obtained, through an 0.2 μm absolute filter, and storage at a temperature of between −20° and −80° C.

Tests with the materials and methods described in the "Test Methods" paragraph below are conducted at the end of each stage.

Stage A: is a batch fermentation process; the inoculum is prepared in an Erlenmeyer flask containing a culture broth formed by a peptone of non-bovine animal origin, such as porcine origin, or a mixture of peptones of non-bovine animal and plant origin, NaCl, CaCl2 and TRIS (tris-hydroxymethyl-aminomethane), at a pH of between 6.9 and 7.4, preferably 7.1. When the optical density measured at 600 nm ($OD_{600nm}$) reaches a value of between 1 and 4, the inoculum is ready for transfer to the fermenter.

The medium used for fermentation is the same as used to prepare the inoculum, with the addition of a small amount of antifoam to prevent foam formation due to aeration and stirring.

One fermentation lasts for 14-20 hours, normally 16 hours. During fermentation, samples are taken by a sterile procedure to check the purity, $OD_{600nm}$, enzyme activity and pH.

When the enzyme activity is ≥25,000 nkat/liter, fermentation is terminated and CaCl$_2$ is added to stabilise the enzyme. The temperature is reduced to approx. 8° C., and the mixture is left under stirring.

The following control tests are performed on the solution obtained at stage A: $OD_{600nm}$; pH; enzyme activity; protein concentration; SDS-PAGE.

The fermentation broth originating from stage A presents, in addition to the collagenase of interest, other proteases produced by the bacterium during fermentation (mainly serine protease), protein aggregates with high molecular weight and residues of the medium.

Stage B: the fermented broth originating from stage A is clarified by tangential flow ultrafiltration (TFF1) with 100-500 kD MWCO cassettes, preferably 300 kD; this eliminates the microbial cells and protein aggregates with high molecular weight.

The following control tests are performed on the solution obtained at stage B: pH; enzyme activity; protein concentration; SDS-PAGE; caseinase assay.

Stage C: the clarified medium originating from stage B is concentrated and dialysed by ultrafiltration with 5-30 kD MWCO cassettes, preferably 10 kD MWCO, approx. 15-25 times. The solution obtained at stage C typically presents enzyme activity of 500-700 nkat/ml, and is stable for 12 months at −20° C. The purpose of tangential flow filtration with 5-30 kD MWCO cassettes is to considerably reduce the volume and replace the culture medium with the 25 mM TRIS-HCl, 10 mM CaCl$_2$, pH 7.1 buffer, which stabilises the collagenase and is suitable for the subsequent purification process.

The following control tests are performed on the solution obtained at stage C: pH; enzyme activity; protein concentration; SDS-PAGE.

Stage D: the solution containing the collagenase deriving from stage C undergoes the first chromatographic purification with anion-exchange resin carrying diethylaminoalkyl groups, preferably diethylaminoethyl, such as DE-52 (diethylaminoethyl cellulose DEAE Whatman). These resins carry weak basic groups and therefore have a degree of ionisation dependent on the pH, with a narrow range of pHs between 6.9 and 7.4, preferably 7.1.

The solution containing the collagenase deriving from stage C is then loaded into a column (Pall Chromatography Column Resolute Mod. 400-V-EP7040) packed with DE-52 resin. The chromatography runs are monitored by a UV-vis detector at 280 nm.

Before the column is loaded it is equilibrated with the same buffer, hereinafter called "equilibration buffer" (25 mM TRIS-HCl, 10 mM CaCl$_2$, pH 7.1), in which the collagenase was dialysed during stage C.

After loading, the resin with the bonded collagenase is eluted with said equilibration buffer, to eliminate the proteins not bonded to the resin. A second wash with a buffer with greater conductivity, hereinafter called "washing buffer" (300 mM TRIS-HCl and 10 mM CaCl$_2$ at pH 7.1), is performed to eliminate impurities with low molecular weight. The collagenase bonded to the resin is eluted by further increasing the conductivity with a third buffer called the "elution buffer" (300 mM TRIS-HCl, 700 mM NaCl and 10 mM $CaCl_2$ at pH 7.1).

Stage E: the fractions collected during elution which present collagenolytic activity and exhibit good purity in SDS-PAGE are combined and transferred to the ultrafiltration system with 10-50 kD MWCO cassettes, preferably 30 kD, to be concentrated and dialysed in a buffer that stabilises the collagenase and is suitable for the subsequent purification process.

The following control tests are performed on the solution obtained at Stage E: pH; enzyme activity; protein concentration; SDS-PAGE; caseinase assay.

Stage F: the solution originating from Stage E passes to the second purification stage with anion-exchange chromatography using a resin carrying strong basic exchanger groups formed by quaternary ammonium, such as Source™ 15Q (GE Healthcare). The chromatography runs are monitored by a UV-vis detector at 280 nm.

Before loading, the column (Millipore GS 70-550) packed with Source™ 15Q resin is equilibrated with the same buffer in which the collagenase was dialysed during stage E (equilibration buffer).

The solution containing the collagenase originating from stage E is loaded into the column, and the resin with the bonded collagenase is eluted with the equilibration buffer to eliminate the unbonded proteins. The collagenase bonded to the resin is eluted by further increasing the conductivity with a second buffer (elution buffer 2-300 mM TRIS-HCl and 10 mM $CaCl_2$ at pH 7.1).

Stage G: the fractions collected during elution which present collagenolytic activity and exhibit a purity of ≥95% in SDS-PAGE are combined and transferred to the ultrafiltration system with 10-50 kD MWCO cassettes, preferably 30 kD, to be concentrated and dialysed in a buffer that stabilises the collagenase.

The following control tests are performed on the solution obtained at Stage G: pH; enzyme activity; protein concentration; SDS-PAGE.

Stage H: the collagenase solution originating from stage G is diluted in stabilising buffer and filtered through an 0.2 µm absolute filter. The sterile solution thus obtained is the final product of the purification process and is analysed for the following characteristics:
protein concentration
enzyme activity
pH
caseinase assay
SDS purity
dimer and high molecular weight analysis with UPLC SEC
endotoxins
sterility tests
Analysis Methods
Spectrophotometric Determination of Enzyme Activity of Collagenase (Wünsch, E., & Heidrich, H. G., Modified)

The present method allows the activity of the collagenase present in aqueous solutions to be determined. The activity is expressed in katals, defined as the quantity of enzyme that catalyses the transformation of 1 mole of substrate in 1 sec under the conditions specified by the method. The quantity of enzyme that catalyses the transformation of the substrate in a pre-set time at 37° C. and pH 7.1, related to the quantity of solution analysed, is expressed in nkat/ml. The principle of the method is based on the reaction between collagenase and the synthetic substrate PZ-L-prolyl-L-leucyl-glycyl-L-prolyl-D-arginine (where PZ=4-phenylazobenzyloxycarbonyl) specific for collagenase. After reacting with collagenase the synthetic substrate is cleaved into 2 fragments, PZ-L-prolyl-L-leucyl and glycyl-L-prolyl-D-arginine. The second fragment is colourless, while the first is a chromophore and can be determined spectrophotometrically after extraction with an organic solution of ethyl acetate acidified with citric acid. The absorbance of the fragment at 320 nm is proportional to the enzyme activity.

To perform the enzymatic assay it is necessary to prepare a series of dilutions of the sample so as to have an enzymatic concentration that falls into the linearity range of the method.

The sample to be analysed is diluted in 25 mM Tris, 10 mM $CaCl_2$, pH 7.1 buffer; 0.5 ml of this buffered solution is reacted at 37° C. for 15 min with 2 ml of a 1.23 mM solution of synthetic substrate. At the end of the enzymatic reaction, 0.5 ml of the reaction mixture is extracted with organic phase with a mixture of 5:1 ethyl acetate and 0.5% citric acid, pH 3.5. The organic phase is removed and dehydrated by adding 300 mg of anhydrous sodium sulphate. The dehydrated organic phase is analysed spectrophotometrically at 320 nm against ethyl acetate. The results of the enzyme activity, expressed in nkat/ml, are calculated with the following formula:

$$\text{Activity } nkat/\text{ml} = \frac{(\text{sample Abs}_{320} - blank\text{Abs}_{320}) \times Std \cdot Conc \cdot (\mu moles/\text{ml})}{Std \text{ Abs}_{320} - \text{blank Abs}_{320}} \times \frac{50 \times 1000}{900} \times fd$$

1000=conversion factor from µmol to nmol
900=seconds in 15 minutes
fd=conversion factor for the initial dilution of the collagenase solution
50=conversion factor for dilution of the sample (0.5 ml and dilute to 2.5 ml. 0.5 ml and dilute to 5 ml)
Std Conc. (µmol/ml)=0.02=0.4 ml of the 250 µM solution diluted to 5 ml.

The blank is given by the same enzymatic reaction as collagenase wherein the solution containing the enzyme is replaced with the reference buffer (25 mM Tris, 10 mM $CaCl_2$, pH 7.1).

The Standard is an 0.2504 mM solution of reaction fragment PZ-L-prolyl-L-leucine in ethyl acetate;

0.4 ml of this solution is added to a solution consisting of 4.6 ml ethyl acetate and 1 ml 0.5% citric acid, pH 3.5. The organic phase is removed and dehydrated by adding 300 mg of anhydrous sodium sulphate. The dehydrated organic phase is analysed spectrophotometrically at 320 nm against ethyl acetate.

Determination of Protein Concentration by the Lowry Method

The protein concentration of solutions containing collagenase is determined by the Lowry method according to the following references:
1. European Pharmacopoeia 5.0, Total Protein, Chapter 2.5.33;
2. Lowry, O. H. et al., 1951, "Protein measurement with the Folin phenol reagent", J. Biol. Chem., 193, 265-275.

UPLC Size Exclusion

UPLC size exclusion analysis is used to determine the dimers and molecules with high molecular weight (defined as impurities) and/or collagenase degradation products. The instrument used is an Acquity UPLC H-Class with PDA eλ detector equipped with an Acquity UPLC BEH 200 SEC column. The analysis is conducted in isocratic mode using a pH 6.4-6.7 phosphate buffer formulated as follows: $Na_2PO_4$ 8.9 g/l, $NaH_2PO_4$ 6.9 g/l and NaCl 8.76 g/l. The buffer is filtered through 0.2 μm absolute filters before use. 1.5-4 μg of protein is injected into a 5 μl volume for each test.

SDS-PAGE Electrophoresis

Electrophoretic analysis on 10% polyacrylamide gel in the presence of sodium dodecyl sulphate (SDS) is conducted according to the Laemmli method (Laemmli, U. K., 1970, "Cleavage of structural proteins during the assembly of the head of bacteriophage T4", *Nature*, 227, 680-685.

Determination of Caseinase

Caseinase determination is used as the method for assaying the aspecific proteases present as impurities in the collagenase solution. The analysis method is performed according to Anson, M. L. (1938) *J. Gen. Physiol.* 22, 79-89, and Folin, O. and Ciocalteu, V. (1927) *J. Biol. Chem.* 73, 627-650. The caseinase is determined using casein as substrate. The reaction can be schematically illustrated as follows:

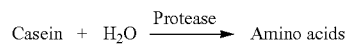

$$\text{Casein} + H_2O \xrightarrow{\text{Protease}} \text{Amino acids}$$

The quantity of tyrosine produced by the reaction is determined colorimetrically by exploiting the reaction with Folin-Ciocalteu reagent, which has the property of oxidising tyrosine in an alkaline environment so that it develops a blue colour. Briefly, 1 ml of solution to be analysed is added to 5 ml of 0.65% (W/V) casein solution and left to react for 30 minutes at 37° C. 0.5 ml of trichloroacetic acid (TCA) is added at the end of incubation, and the sample is filtered through 0.45 μm filters after 2 minutes. The filtrate is collected; 5 ml of 0.5 M $Na_2CO_3$ and 1 ml of 0.5 N Folin-Ciocalteu are added and the mixture is left to react for 30 minutes at 37° C. At the end of the reaction the sample is further filtered through 0.45 μm filters and the filtrate is analysed with the spectrophotometer, measuring the absorbance at a wavelength of 660 nm. At the same time the blank and the calibration line are prepared with a solution of 1.1 mM L-tyrosine as standard.

The results are calculated with the following formula:

$$\frac{\text{Unit}}{\text{ml}} = \frac{\frac{(O.D._{\text{sample}} - O.D._{\text{blank}}) - c}{m} \times 10 \times 6.5 \times 8}{1 \times 2} \times fd$$

c=known term
m=angular coefficient
10=conversion factor from 30 minutes to 5 hours
6.5=total volume in ml of stop solution
8=total volume of colorimetric solution
1=ml of collagenase sample
2=ml of sample used for colour development
fd=dilution factor Measurement of Optical Density $OD_{600nm}$ This method allows the growth of the cells during the various stages of the production process to be evaluated, from the 5-liter Erlenmeyer flask to the 1000-liter bioreactor. To perform the $OD_{600nm}$ measurement, 1 ml of cell suspension is taken up and centrifuged at 12000 rcf for 5 min, the supernatant is eliminated and the cells resuspended in 1 ml of distilled $H_2O$, after which the absorbance is read at 600 nm.

Endotoxin Assay

The endotoxin assay in the final collagenase solution is performed as described in the European Pharmacopoeia, Endotoxin Test, Chapter 2.6.14.

Determination of Enzyme Activity of Collagenase by UPLC

The present method allows the activity of collagenase to be quantified by UPLC analysis. The method is based on quantification of the fragment produced by the enzymatic reaction (according to the Wünsch method) against the external standard.

The quantity of enzyme that catalyses the transformation of the substrate in a pre-set time at 37° C. and pH 7.1, related to the quantity of solution analysed, is expressed in nkat/ml. The activity is expressed in katals, defined as the quantity of enzyme that catalyses the transformation of 1 mole of substrate in 1 sec under the conditions specified by the method.

The range of use of the method in linear conditions extends to approx. 1.2 nkat/ml, as the maximum activity of collagenase in solution analysable according to the methodology described, with no need to perform "dilutions".

The aqueous solution of collagenase is reacted with the synthetic substrate PZ-L-prolyl-L-leucyl-glycyl-L-prolyl-D-arginine (where PZ=4phenylazobenzyloxycarbonyl). Two fragments are released under controlled conditions (pH, temperature, time): PZ-L-prolyl-L-leucine; glycyl-L-prolyl-D-arginine. The second fragment is determined by UPLC.

The operating parameters of the UPLC system are:
flow rate: 0.919 ml/min
duration of run: 3 minutes
wavelength: 320 nm
injection volume: 1.4 μl
column temperature: 25° C.

| time (minutes) | Citric acid 0.5% w/v pH 3.5 | Acetonitrile |
|---|---|---|
| 0 | 50 | 50 |
| 1.17 | 50 | 50 |
| 0.34 | 10 | 90 |
| 1.13 | 10 | 90 |

Under these conditions the substrate elutes after approximately 0.25 minutes and the fragment after approx. 0.44 minutes The determination of the enzyme activity consists of the following steps:
I. Preparation of a 25 mM TRIS-HCl, 10 mM $CaCl_2$, pH 7.1 buffer solution (Reagent A).
II. Preparation of an 0.5% citric acid solution (Reagent B).
III. Preparation of a 1.23 mM substrate solution (Reagent C).
IV. Preparation of the solution of PZ-L-prolyl-L-leucine 200 μM in acetonitrile (reagent E).
V. Preparation of solution of collagenase to be analysed (solution D). The enzymatic solution is diluted in a volumetric flask with the buffer solution (Reagent A), to obtain a solution with activity less than 1.2 nkat/ml.
VI. Enzymatic reaction. 2 ml of reagent C and 0.5 ml of solution D are pipetted into a screw-cap test tube using a glass pipette. The mixture is left to react for 15 min at 37° C. in a thermostatic bath. At the end of the reaction, this is called solution Y. A "blank", W, is prepared in parallel as follows: 2 ml of reagent C and 0.5 ml of buffer solution (reagent A). The mixture is left to react for 15 min at 37° C. in a thermostatic bath.

VII. The samples are prepared by taking up 0.5 ml of solution Y and introducing it into a 10 ml flask containing 2.0 ml of 0.5% citric acid, and made up to volume with acetonitrile.

VIII. The reference solution is prepared by introducing 0.5 ml of blank W, 2.0 ml of citric acid and 1.5 ml of reagent E into a 10 ml flask, and making it up to volume with acetonitrile.

IX. 1.4 µl of the reference solution followed by 1.4 µl of the solution to be analysed are injected.

The results of the enzyme activity expressed in nkat/ml are calculated with the following formula:

$$\text{Activity } nkat/\text{ml} = \frac{\text{Sample Area} \times \text{Standard } Conc \cdot (\mu\text{moles/ml})}{\text{Standard Area}} \times \frac{1000 \times 100}{900} \times fd$$

Calculation of enzyme activity=nanomoles per second per ml of solution (nkat/ml), where:
1000=conversion factor from micromoles to nanomoles
100=conversion factor for dilution of sample (0.5 ml to 2.5 ml. 0.5 ml to 10 ml)
900=seconds in 15 minutes
Standard Conc. (µmoles/ml)=0.03 (1.5 ml of the 200 µM solution to 10 ml)
fd=dilution factor of the collagenase solution used to prepare solution
D Characterisation of Protein
Determination of N-Terminal Sequence The N-terminal amino-acid sequence of the collagenase originating from *Vibrio alginolyticus* chemovar. *Iophagus* was determined by the Edman degradation method using a liquid-phase automated protein sequencer (ABI-Perkin Elmer mod. 477°). The sequence obtained was verified by bioinformatic analysis, running BLAST (Basic Logical Alignment Search Tool) searches of the sequence against the entire GENBANK database.

Peptide Mapping analysis

Figure 1:
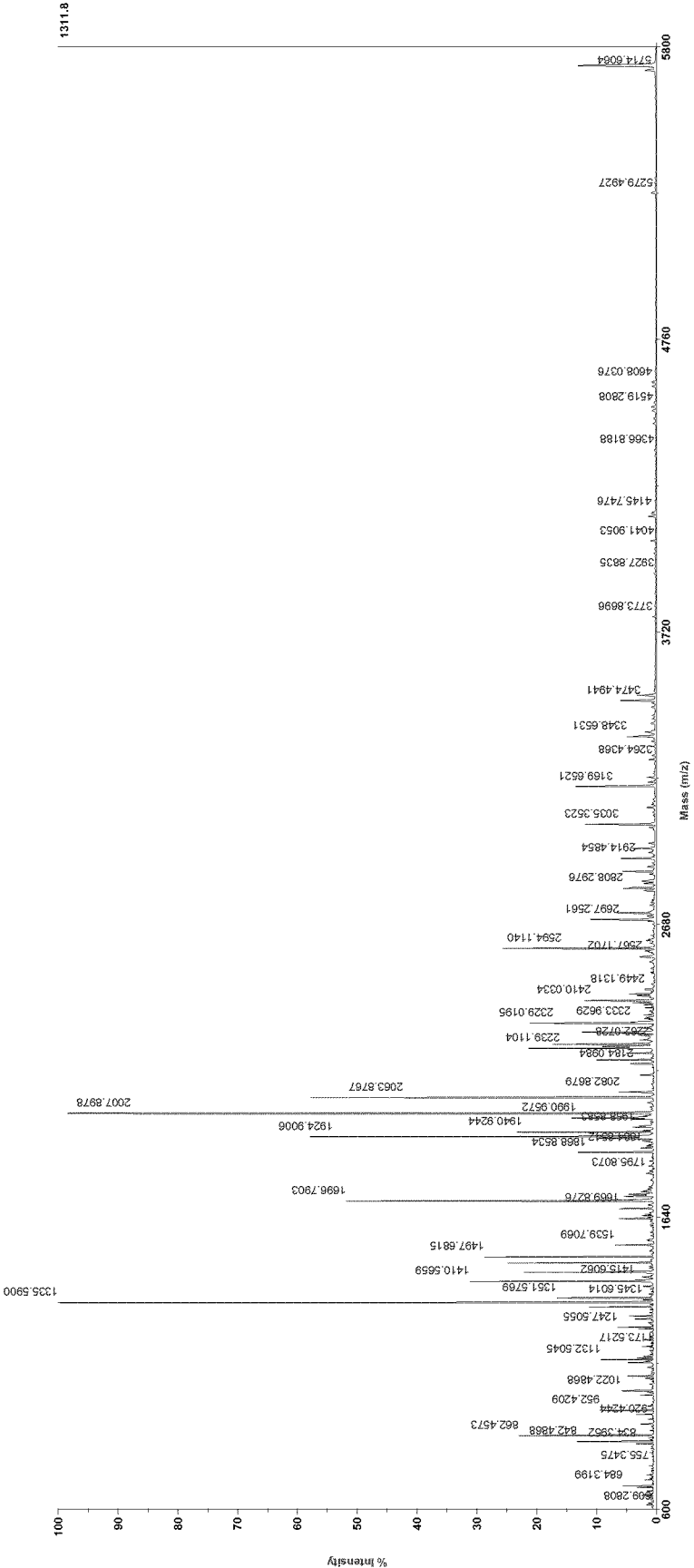
FIG. 1 is a global spectrum of a tryptic digest analysis.

To analyse the peptide map, the collagenase is first reduced with DTT, alkylated with iodoacetamide and then desalted using a PD10 column, eluting with 1% acetic acid. The eluate is subjected to tryptic digestion, and the fragments are analysed with MALDI-MS. The global spectrum is reported in (FIG. 1: tryptic digest analysis); this enabled us to establish that over 90% of the amino-acid sequence is identical to the sequence deposited in the database corresponding to the collagenase produced from *Vibrio alginolyticus* chemovar *Iophagus*.

Circular Dichroism

The far-UV circular dichroism (FUV-CD) spectra were recorded on a Jasco spectrum polarimeter, model J-810, connected to a bath thermostated at 25° C. The spectra were recorded using an 0.1 cm cuvette at the speed of 20 nm/min, with a response every 8 sec, for an average of two accumulations. Each sample was tested in duplicate.

The CD signal was expressed as ellipticity per mean residue, calculated with the formula [θ]=θobs×MRW/(10× 1×c), wherein θobs is the ellipticity observed in mdeg, "MRW" is the mean molecular weight per residue, "l" is the optical path in cm and "c" is the concentration in mg/ml. The samples were analysed at the concentration of 0.2 mg/ml.

Figure 2:
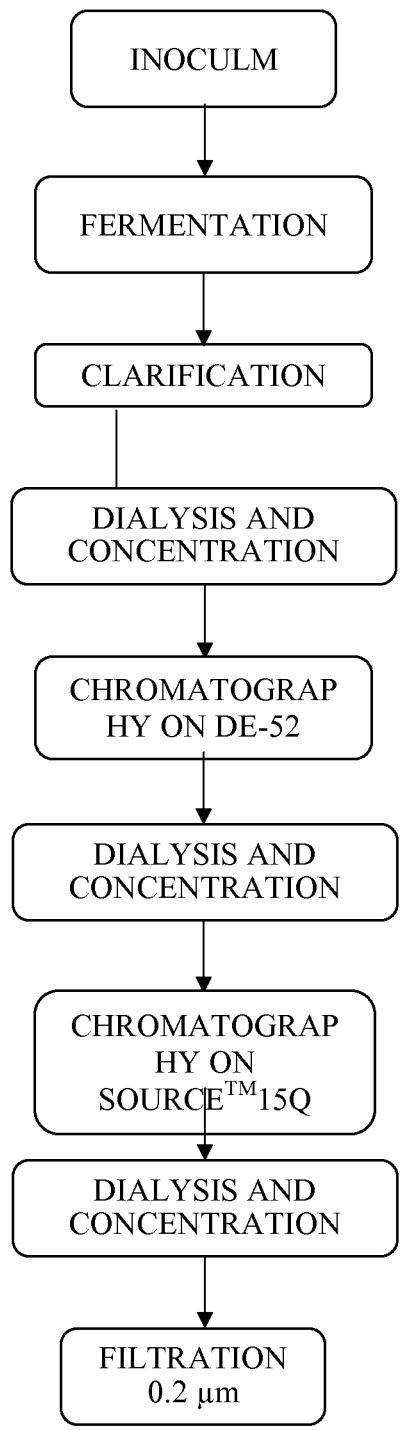
FIG. 2 is a flow chart of the production and purification process of the present invention.

Example 1: Production and Purification of Collagenase from *Vibrio alginolyticus* chemovar. *Iophagus*, in an 800 L fermentation (FIG. 2: Flow chart of production and purification process)

Fermentation

Fermentation is divided into 2 stages:
Stage 1: Preparation of inoculum
Stage 2: Fermentation Stage 1: The culture medium is liquid, and consists of a solution of 1.21 g/l TRIS, 23.4 g/l NaCl, 0.29 g/l $CaCl_2$ and 15 g/l peptone of non-bovine animal origin (porcine, or a mixture with peptones of porcine and plant origin) dissolved in distilled water (Millipore milliQ). The pH of the medium is adjusted to 7.1 with HCl and sterilised in the autoclave at a temperature of ≥122° C. for 30 min. A 1.5 ml ampoule of *Vibrio alginolyticus* chemovar. *Iophagus* (WCB-Working Cell Bank) is inoculated into a 5 L Erlenmeyer flask containing 2 L of culture medium and incubated at 30° C. with stirring at approx. 150 rpm, for a time ranging between 8 and 16 hours. When the $OD_{600nm}$ reaches a value of between 1 and 4, the inoculum is ready to be transferred to the fermenter.

Stage 2: the culture medium is the same as used for Stage 1, with the addition of 0.25 g/l of Sigma 204 antifoam, sterilised at ≥122° C. for 30 min in the fermenter. The 2 L of inoculum is transferred by a sterile procedure to the fermenter containing 800 L of fermentation broth, and the fermentation parameters are set as follows:
temperature 30° C.±1° C.,
stirring 50-150 rpm,
air 10-80 $Nm^3/h$,
dissolved oxygen>50%,
pH 7.1±0.1,
pressure 0-0.4 bar.

A typical fermentation lasts for 14-20 hours, normally 16 hours, which corresponds to the highest level of collagenase enzyme activity throughout the fermentation process. During fermentation, samples are taken by a sterile procedure to check the purity of the culture, the $OD_{600nm}$ and enzyme activity. The activity of the collagenase is determined spectrophotometrically by the modified Wünsch-Heidrich method (Wünsch, E. & Heidrich, H. G. 1963).

When the enzyme activity is ≥25,000 nkat/liter, fermentation is terminated and $CaCl_2$ is added, up to a final concentration of 1.47 g/l, to stabilise the enzyme. The temperature is lowered to approx. 8° C., and the mixture is left under stirring for approx. 10-30 minutes. Typically, a fermented broth has the following characteristics:
1) Enzyme activity between 25,000 and 50,000 nkat/liter
2) $OD_{600nm}$ between 5 and 8
3) Absence of microbial contaminants Clarification: TFF1 Ultrafiltration with 300 kD MWCO (Molecular Weight Cut-Off) Cassettes The fermentation broth, approx. 800 liters, is transferred to the ultrafiltration system containing SARTOCON II holder (Sartorius) where five 300 kD MWCO cassettes (Code 3021467907E-SG) are housed, each with a filtration area of 0.5 $m^2$. The filtration membrane is made of modified PolyEtherSulphone (PES), the main characteristic of which is a low affinity for proteins, allowing >80% recovery and clarification of the medium with low loss of collagenase.

The objective of ultrafiltration with 300 kD cassettes is to remove the microbial mass from the fermentation broth and eliminate a protein aggregate of approx. 320 Kda.

Dialysis and Concentration: TFF2 Ultrafiltration with 10 kD MWCO Cassettes

Figure 3:
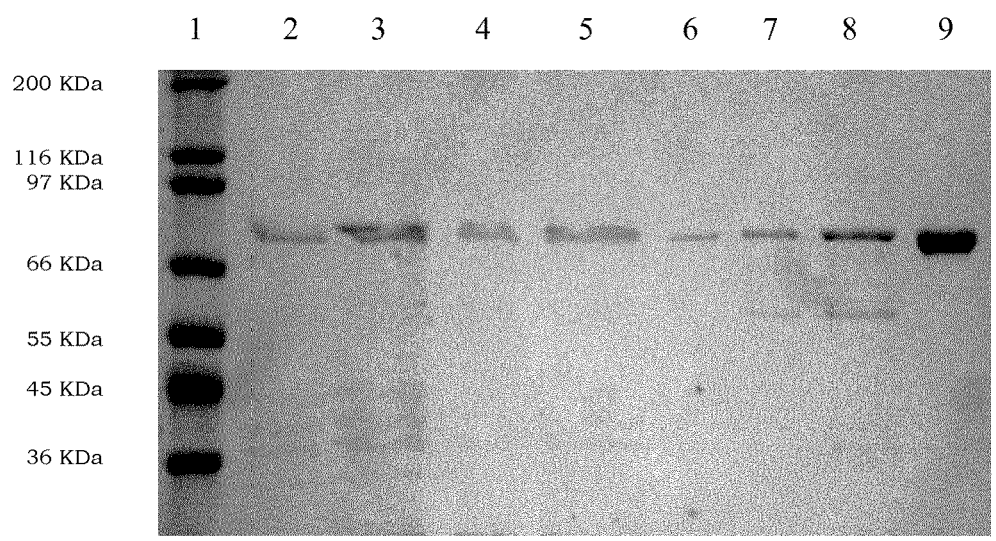
FIG. 3 is a SDS-PAGE of the 300K and 10K ultrafiltration stages of the present invention.

After clarification the medium is concentrated and dialysed in the PALL Mod UF-A-P0971 ultrafiltration system in which six 10 kD MWCO cassettes (Code 34293012R), each with a filtration area of 0.5 m², are housed. The filtration membrane is made of modified PolyEtherSulphone (PES), the main characteristic of which is a low affinity for proteins, allowing >80% recovery. Ultrafiltration with 10 kD cassettes allows the volume to be reduced 15-25 times, low molecular weight contaminants to be eliminated, and the culture medium replaced with 25 mM TRIS, 10 mM $CaCl_2$, pH 7.1 buffer, which is suitable for the subsequent purification process. After the ultrafiltrations, the following analyses are performed:
1) Enzyme activity
2) Protein assay
3) SDS-PAGE (FIG. 3: SDS-PAGE of the 300K and 10K ultrafiltration stages)
Legenda of FIG. 3
Lane 1 High Range SigmaMarker™
Lane 2 10 µl fermentation broth
Lane 3 20 µl fermentation broth
Lane 4 10 µl TFF 300K filtrate
Lane 5 20 µl TFF 300K filtrate
Lane 6 2 µl TFF 10K retentate
Lane 7 5 µl TFF 10K retentate
Lane 8 16 µl TFF 10K retentate
Lane 9 2 µg FIDIA collagenase
Weak Anionic Chromatography (Whatman DE-52)

The solution containing the collagenase deriving from the ultrafiltration processes is the starting material for the first purification by weak anion-exchange chromatography using DE-52 resin (Whatman DEAE: diethylaminoethyl cellulose).

The chromatography runs are monitored by a UV-vis detector at 280 nm. Typically, 10-25 liters of the solution containing collagenase with a protein concentration of 0.8-1.2 g/l are loaded into the column (Pall Chromatography Column Resolute Mod. 400-V-EP7040) packed with 10 Kg of DE-52 resin. The quantity of total proteins loaded into the column is 0.8-3 g/Kg of resin. The resin is equilibrated with 10 column volumes (BV) of 25 mM TRIS-HCl and 10 mM $CaCl_2$ at pH 7.1, hereinafter called "equilibration buffer".

After loading, the resin with the bonded collagenase is eluted with 2-4 BV, generally 2, of equilibration buffer to eliminate the proteins not bonded to the resin and restore the conductivity values to those prior to loading of the sample.

To eliminate the low molecular weight impurities, a further elution is performed with 3-5 BV, generally 4, of a buffer formulated as follows: 300 mM TRIS-HCl and 10 mM $CaCl_2$ at pH 7.1 (washing buffer). The collagenase bonded to the resin is eluted by increasing the conductivity with 3-5 BV, generally 4, of a third buffer composed as follows: 300 mM TRIS-HCl, 700 mM NCl and 10 mM $CaCl_2$ at pH 7.1 (elution buffer).

The fraction collected during elution with the elution buffer is subjected to an enzyme activity assay and analysed with SDS-PAGE.

Figure 4:
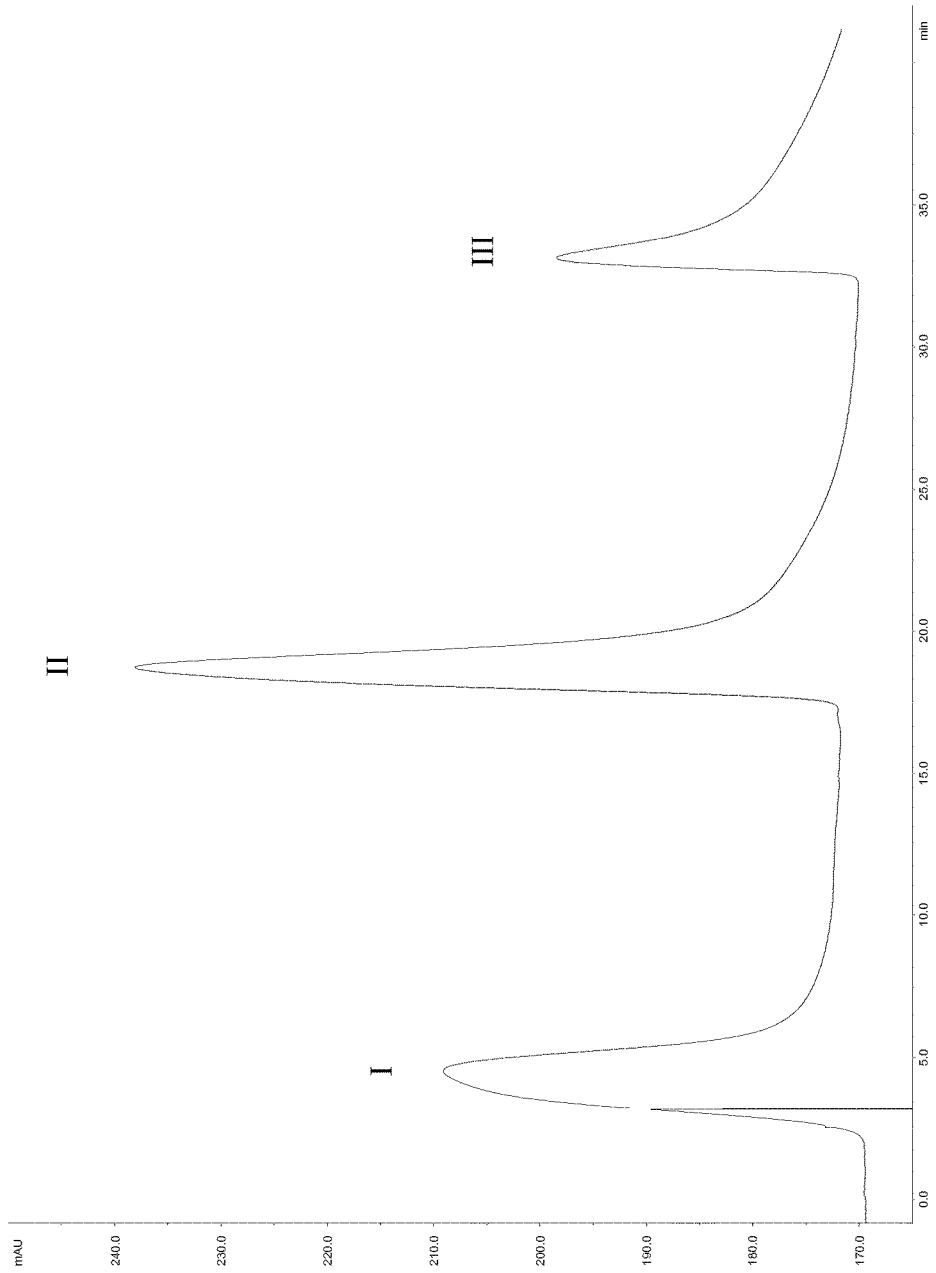
FIG. 4 is a typical chromatogram of a DE-52 resin.

A typical chromatographic profile presents three distinct peaks, as shown in FIG. 4 (typical chromatogram of DE-52):
the first (I) (peak eluted with equilibration buffer) corresponds to the unbonded proteins, which presents no enzyme activity.
the second peak (II) corresponds to the elution with the washing buffer, which presents collagenolytic activity but is discarded because numerous impurities are also present.
the third peak (III) corresponds to elution with the elution buffer, and is the peak with the greatest enzyme activity and highest purity.

Figure 5:
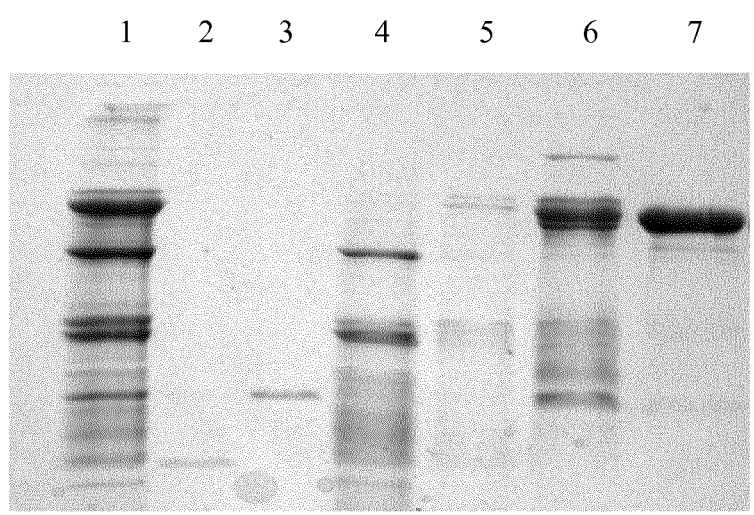
FIG. 5 is a SDS-PAGE of a peak from a typical chromatogram of a DE-52 resin containing collagenase.

Typically, the peak containing collagenase has a volume of 18-22 liters, and is analysed for the following characteristics:
1) Enzyme activity
2) Protein assay
3) SDS-PAGE (FIG. 5)
Legenda of FIG. 5
Lane 1 5 µl of sample after TFF2
Lane 2 20 µl unbonded
Lane 3 10 µl peak I fraction 1
Lane 4 10 µl peak I fraction 2
Lane 5 10 µl peak II fraction 1
Lane 6 10 µl peak II fraction 2
Lane 7 10 µl peak III
Dialysis and Concentration: TFF3 Ultrafiltration with 30 kD MWCO Cassettes The fraction corresponding to the third chromatographic peak is concentrated and dialysed in the Cogent™ (Millipore) ultrafiltration system in which two 30 k MWCO cassettes (Code 31158044R), each with an 0.1 m² filtration area, are housed. The filtration membrane is made of PolyEtherSulphone (PES) whose main characteristic is a low affinity for proteins, allowing recovery >95%. Ultrafiltration with 30 kD cassettes allows the volume to be reduced 3-6 times and the elution buffer from DE-52 to be replaced with 25 mM TRIS, 10 mM $CaCl_2$, pH 7.1 buffer, which is suitable for the subsequent purification process. The following controls are performed on the ultrafiltrate:
1) Enzyme activity
2) Protein assay
Strong Anionic Chromatography (Source™ 15Q GE Healthcare).

The collagenase solution originating from TFF3 is the starting material for the second purification by strong anion-exchange chromatography using Source™ 15Q resin (GE Healthcare). The chromatography runs are monitored by a UV-vis detector at 280 nm. Typically, 3-6 liters of solution containing collagenase with a protein concentration of 0.8-1.2 mg/ml are loaded into a column (Millipore GBP 70-550) packed with 100-200 ml of Source™ 15Q resin; the quantity of total proteins loaded into the column amounts to 24-36 mg/ml of resin. Before loading, the resin is equilibrated with 2 column volumes (BV) of 10 mM TRIS-HCl and 10 mM $CaCl_{25}$ at pH 7.1, called the "equilibration buffer".

Figure 6:
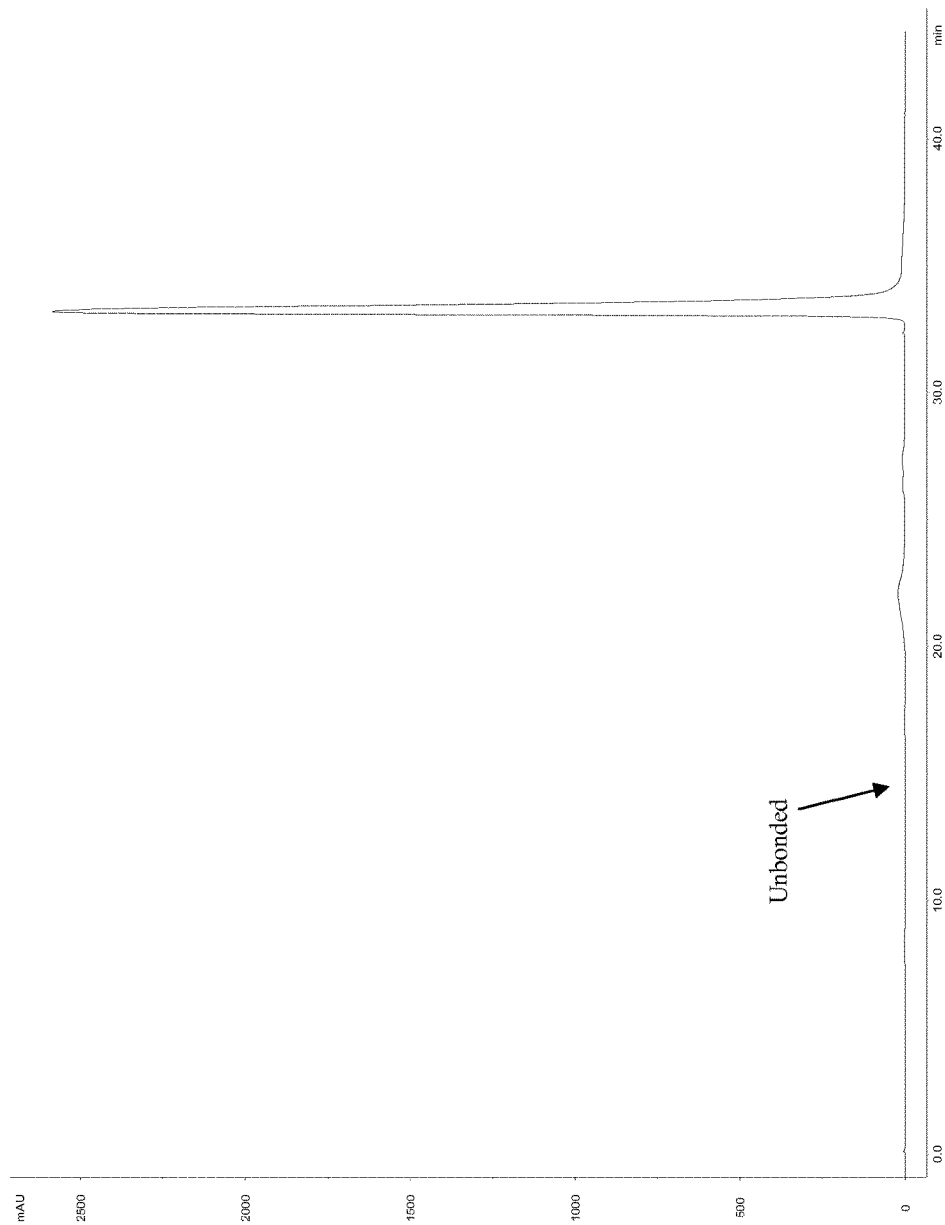
FIG. 6 is a typical chromatogram of Source™ 15Q.

After loading, the resin with the bonded collagenase is eluted with 5-7 BV of equilibration buffer to eliminate the unbonded proteins and restore the conductivity to the initial values. The collagenase bonded to the resin is eluted with 5-10 BV of 300 mM Tris-HCl and 10 mM $CaCl_2$ at pH 7.1 (elution buffer). The fraction containing collagenase is eluted in a single peak, typically of 1-2 liters, which can be seen in the chromatogram shown in FIG. 6 (Typical chromatogram of Source™ 15Q).

Figure 7:
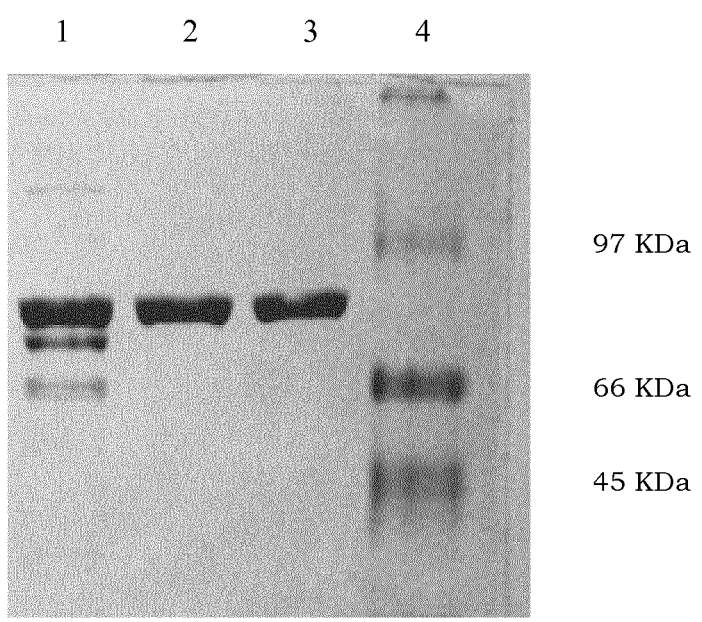
FIG. 7 is a SDS-PAGE of a fraction of Source™ 15Q.

The fraction containing the collagenase collected during elution is subjected to the following controls:
1) Enzyme activity
2) Protein assay
3) SDS-PAGE (FIG. 7: SDS-PAGE of Source Fractions™ 15Q)

Legenda of FIG. 7:
Lane 1 20 µl unbonded conc. 20×
Lane 2 10 µl Fraction 1
Lane 3 10 µl Fraction 2
Lane 4 LMW Dialysis and Concentration: TFF4 Ultrafiltration with 30 kD MWCO Cassettes The fraction containing collagenase is transferred to the Cogent™ (Millipore) ultrafiltration system in which two 30 kD MWCO cassettes with PolyEtherSulphone (PES) membrane, each with an 0.1 m² filtration area, are housed. This ultrafiltration step allows the sample to be dialysed and concentrated against the 25 mM TRIS-HCl and 10 mM $CaCl_2$ pH 7.1 buffer.

Filtration and Storage

The solution originating from TFF4 is filtered through 0.2 µm PolyEtherSulphone (PES) absolute filters for final sterilisation of the product. The end product is stored in specific containers at −20° C.

The collagenase solution thus obtained is analysed for the following characteristics: protein concentration; enzyme activity; pH; aspecific protease assay; SDS-PAGE purity (FIG. 8: SDS-PAGE of final product); UPLC SEC purity (dimer and high molecular weight analysis); LAL Test for determination of endotoxins (according to the European Pharmacopoeia, the product must contain no more than 5 IU/kg/hour).

Figure 8:
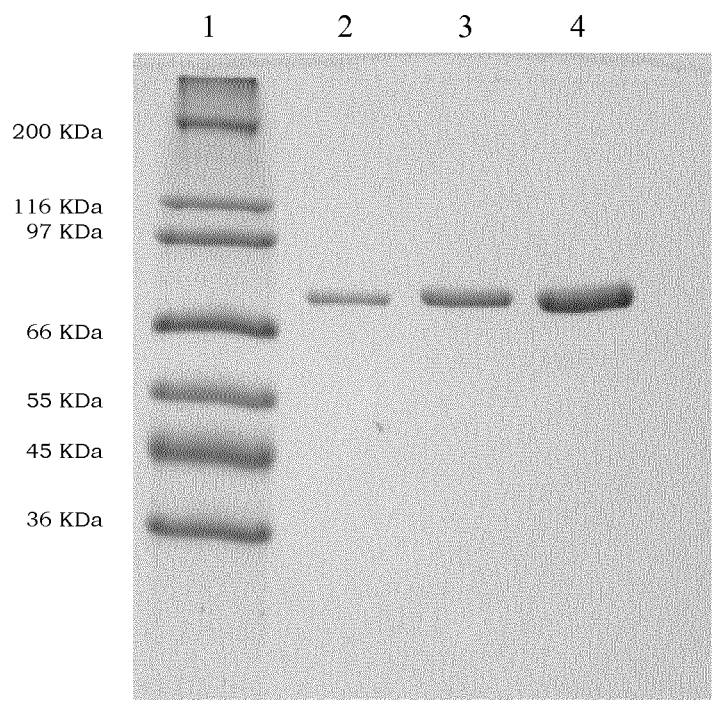
FIG. 8 is a SDS-PAGE of the final product of the present invention.

Legenda of FIG. 8:
Lane 1 HMW
Lane 2 Fidia Collagenase 0.5 µg/lane
Lane 3 Fidia Collagenase 1 µg/lane
Lane 4 Fidia Collagenase 2 µg/lane The specific characteristics are summarised in Table below.

TABLE

| TEST | SPECIFICATIONS |
| --- | --- |
| Identification: UPLC size exclusion | positive |
| Appearance | Clear, colourless solution in 25 mM TRIS-HCl, 10 mM $CaCl_2$, pH 7.1 |
| pH of solution | 7.1 ± 0.2 |
| Protein concentration | ≤1.0 mg/ml of solution |
| Specific activity | 1000-1800 nkat/mg |
| Caseinase activity | <1.0 U/ml |
| Purity in UPLC | 98.0-100% |
| Identification | Molecular weight 82 KDa |
| Purity in SDS-PAGE | 98.0-100% |
| Endotoxins | Absent or conforming to European Pharmacopoeia |

The collagenase produced and purified according to the present invention has been tested by the Applicant to verify the following characteristics, with the results set out below:
pure: has a purity of between 98 and 100%;
free of microbial and protein contaminants (endotoxins, DNA);
stable at a pH of between 5.5 and 11 (established by enzymatic test)
stable in aqueous solution, for example comprising 25 mM TRIS-HCl, 10 mM $CaCl_2$, pH 7.1, at a T of between 4° and 40° C., particularly stable a 37° C.
stable in aqueous solution at 4° C. for 30 days;
stable in aqueous solution at a T of between −20° C. and −80° C. for 24-48 months
can be freeze-dried with suitable excipients (described below) to obtain a stable lyophilic powder.

The lyophilisate of collagenase, which is a further subject of the present invention, is prepared with excipients particularly suitable to maintain its stability, and can preferably contain:
maltose: 95-96%, preferably 95.75%;
salts (such as TRIS-HCl+$CaCl_2$): 1.0-1.5%, preferably 1.3%;
collagenase: 2.5-3.5%, preferably 2.95%, to obtain a freeze-dried powder with enzyme activity between 7-20 nkat/mg of powder The quantities indicated above for collagenase lyophilisate are percentages by weight compared with the total weight of the lyophilisate.

The collagenase obtained according to the production and purification process is therefore suitable for the preparation of pharmaceutical compositions of various types, and is designed, as stated, for the use in the treatment of disorders characterised by collagen accumulation or dermocosmetic treatment of blemishes/imperfections that benefit from a reduction in local collagen accumulations. The most frequent applications relate to topical and/or local treatment of burns of different degrees, scalds, bedsores, vascular ulcers and diabetic ulcers; in these cases, collagenase effectively eliminates the eschar, thus allowing the viable underlying cells to activate for the purpose of the repair process. Other therapeutic applications relate to cellulitis, post-surgical adhesions, hypertrophic scars and keloids; in these situations, abnormal collagen production has adversely affected the normal repair process, and they can benefit from lysis of the irregularly accumulated collagen.

Other disorders treatable with collagenase are adhesive capsulitis (frozen shoulder), Dupuytren's contracture and Peyronie's disease.

Topical or systemic application, in particular injectable application, may be required, depending on the disorder.

As regards topical applications, the surprising stability in aqueous solution of the enzyme claimed herein allows its formulation in hydrophilic carriers; in particular, it has been found that collagenase can be formulated with particular polymers which hydrate in contact with the exudate of the lesion on which it is placed, giving rise to a gel. In this situation, the enzyme is released gradually and in larger quantities than obtained with the ordinary lipophilic carriers used to date, producing a better therapeutic effect; the number of daily applications can also be reduced, thus improving the patient's compliance. The topical pharmaceutical form preferred in the ambit of the present invention is dusting powder, the industrial preparation of which does not require any particular processes and which, in the form of a pharmaceutical preparation, can easily be measured, correctly deposited within the edges of the lesion, and stored for long periods. The hydrophilic polymer used must be able to absorb the fluid produced by the wound rapidly, producing an adherent gel material. Said gel must obviously have viscosity characteristics which allow its residence on the wound bed; an excessively solid gel tends to vitrify, while an excessively liquid gel slides off the wound bed, carrying the active ingredient with it. Moreover, as the preparation must be sterile, it is essential for the polymer selected to maintain its rheological properties after hydration, even when previously sterilised by common means (usually γ rays). To identify the most suitable polymer, the Applicant has conducted a series of tests on numerous polymers (starch and derivatives, alginates, cellulose derivatives, polyvinyl alcohols and derivatives, gums and pectins), as briefly described herein. A continuous film of saline solution 2.5 mm thick was created in a glass Petri dish with a diameter of 5 cm, on which the powdered polymer to be examined (approx. 1 g) was sprinkled from a steel sieve with pores of fixed size. Further liquid was added as long as the polymer, converted to a gel, was able to absorb it, maintaining a viscosity such that it did not drip from the dish when held vertically. After the absorption rate of the liquid and the transparency and consistency of the gel obtained were evaluated, it was decided that the most suitable polymer for the purpose of the present invention is corn starch glycolate.

Corn starch glycolate is a fine white, flowable, very hygroscopic powder, used in the manufacture of tablets and capsules due to its disintegrating properties, but has never been used by direct application. Corn starch glycolate has a pH of between 5.5 and 7.5, i.e. similar to that of the tissue on which it is applied, and swells in water to up to 300 times its volume.

In addition to the collagenase enzyme, the dusting powder can also contain a further active ingredient, which stimulates cell migration in order to allow more rapid re-epithelialisation of the wound bed, and therefore more rapid closing of the wound. Of the various possible agents, hyaluronic acid is particularly suitable for these purposes; it is a heteropolysaccharide consisting of alternating residues of D-glucuronic acid and N-acetyl-D-glucosamine. It is a straight-chain polymer with a molecular weight ranging between 50,000 and $13 \times 10^6$ Da, depending on the source from which it is obtained and the preparation methods used. The HA used in the present invention can derive from any source, such as extraction from cockscombs (EP 138572 B1), fermentation (from *Streptococcus*), or biosynthesis (from *Bacillus*), and have a mean molecular weight of between 400 and $3 \times 10^6$ Da, in particular between $1 \times 10^5$ Da and $1 \times 10^6$ Da, and even more particularly between 200,000 and 750,000 Da. Preferably, the HA used herein for topical applications has a mean molecular weight (MW) of between 130 and 230 kDa, preferably between 145 and 210 kDa, and even more preferably between 160 and 200 kDa; the latter will hereinafter be called HA with mean MW 200 kDa. HA with a mean molecular weight of between 200 and 1800 kDa, preferably between 500 and 1300 kDa, and even more preferably between 750 and 1200 kDa, is used for injectable applications. References to mean molecular weight refer to the weight-average MW, calculated by the intrinsic viscosity method (Terbojevich et al., *Carbohydr Res*, 1986, 363-377).

HA is found in nature in pericellular gels, in the ground substance of the connective tissue of vertebrates (of which it is one of the main components), in the synovial fluid of the joints, the vitreous humor and the umbilical cord.

It has been demonstrated that HA plays a crucial role in the tissue repair process both in structural terms (in organising extracellular matrix and regulating its hydration) and as a substance that stimulates a wide range of processes in which it is directly and indirectly involved (clot formation, phagocytic activity, fibroblast proliferation, neovascularisation, re-epithelialisation, etc.) (Weigel P. et al., *J Theoretical Biol*, 1986:219-234; Abatangelo G. et al., *J Surg Res*, 1983, 35:410-416; Goa K. et al., *Drugs*, 1994, 47:536-566). The role of HA in the preparations described herein is not only to promote wound-healing, but above all to prevent the collagenase that collects at the edges of the wound from damaging the living, healthy cells that reside there by preventing their migration towards areas that need regeneration. Moreover, the presence of HA, which is also an absorbent polymer, aids the formation of the gel on the wound bed and improves the release, and therefore the enzyme activity, of collagenase, as has been demonstrated and will be illustrated below.

The formulations identified can also include an agent that promotes the glide of the powders at the mixing stage; those most commonly used include colloidal silicon dioxide, which can optionally be included in quantities ranging 0.1 and 3%, preferably between 0.2 and 1%, as known to the skilled person.

In the ambit of the present invention the Applicant consequently intends to claim pharmaceutical compositions for topical use in the form of dusting powder, comprising:
  collagenase obtained by the process described above, in a quantity equivalent to an activity of between 2 and 8 nkat/g of the finished product, preferably 5 nkat/g of the finished product;
  optionally, HA with a weight average molecular weight ranging between 130 and 230 kDa, preferably between 145 and 210 kDa, and even more preferably between 160 and 200 kDa, in a quantity ranging between 0.1 and 5%, preferably between 0.2 and 2%;
  optionally, colloidal silicon dioxide in a quantity of between 0.1 and 3%, preferably between 0.2 and 1%;
  corn starch glycolate, in the quantity required to complete the percentage composition.

The quantities indicated above for the dusting powder are percentages by weight compared with the total weight of the composition.

Some examples of preparation of the pharmaceutical compositions disclosed above will now be described by way of example but not of limitation.

Example 2: Preparation of a Dusting Powder Containing Collagenase, Hyaluronic Acid (HA) and Corn Starch Glycolate (Formulation 1)

The collagenase, in lyophilic form, is measured so that it corresponds to an activity of 5 nkat/g of finished product.

| | |
|---|---|
| Collagenase | equivalent to 5 nkat/g |
| 200 kDa mean MW HA | 0.2 g |
| Corn starch glycolate | q.s. for 100 g |

About half the quantity of gelling polymer is weighed and introduced into the container; the collagenase and HA, previously micronised and sieved at 50μ, are weighed and introduced into the container. Finally, the remaining quantity of gelling polymer is weighed and introduced into the container. The preparation is performed by direct mixing of the powders in a parallelepipedal polyethylene vial closed with a polyethylene sub-cap and a polypropylene screw cap, with a sufficient capacity to leave at least 40-50% of empty headspace. The vial, fixed in the arm of a V mixer in an oblique position (45 degrees), rotates obliquely about its minor axis at the speed of 50 rpm. Mixing proceeds until the mixture is homogenous.

Example 3: Preparation of a Dusting Powder Containing Collagenase, Hyaluronic Acid (HA), Corn Starch Glycolate and Glidant (Formulation 2)

The collagenase, in lyophilic form, is measured so that it corresponds to an activity of 5 nkat/g of finished product.

| | |
|---|---|
| Collagenase | equivalent to 5 nkat/g |
| 200 kDa mean MW HA | 0.2 g |
| Colloidal silicon dioxide | 0.2 g |
| Corn starch glycolate | q.s. for 100 g |

About half the quantity of gelling polymer is weighed and introduced into the container; the collagenase and HA, previously micronised and sieved at 50μ, are weighed and introduced into the container. Finally, the remaining quantity of gelling polymer and the glidant are weighed and introduced into the container. The preparation is performed by direct mixing of the powders in a parallelepipedal polyethylene vial closed with a polyethylene sub-cap and a polypropylene screw cap, with a sufficient capacity to leave at least 40-50% of empty headspace. The vial, fixed in the arm of a V mixer in an oblique position (45 degrees), rotates obliquely around its minor axis at the speed of 50 rpm. Mixing proceeds until the mixture is homogenous.

Example 4: Preparation of a Dusting Powder Containing Collagenase, Hyaluronic Acid (HA), Corn Starch Glycolate and Glidant (Formulation 3)

The collagenase, in lyophilic form, is measured so that it corresponds to an activity of 5 nkat/g of finished product.

| | |
|---|---|
| Collagenase | equivalent to 5 nkat/g |
| 200 kDa mean MW HA | 0.2 g |
| Colloidal silicon dioxide | 1 g |
| Corn starch glycolate | q.s. for 100 g |

For preparation, see Example 2.

Example 5: Preparation of a Dusting Powder Containing Collagenase and Corn Starch Glycolate (Formulation 4)

The collagenase, in lyophilic form, is measured so that it corresponds to an activity of 5 nkat/g of finished product.

| | |
|---|---|
| Collagenase | equivalent to 5 nkat/g |
| Corn starch glycolate | q.s. for 100 g |

Approx. half the quantity of gelling polymer is weighed and introduced into the container; the collagenase is weighed and introduced into the container. Finally, the remaining quantity of gelling polymer is weighed and introduced into the container. The preparation is performed by direct mixing of the powders in a parallelepipedal polyethylene vial closed with a polyethylene sub-cap and a polypropylene screw cap, with a sufficient capacity to leave at least 40-50% of empty headspace. The vial, fixed in the arm of a V mixer in an oblique position (45 degrees), rotates obliquely around its minor axis at the speed of 50 rpm. Mixing proceeds until the mixture is homogenous.

Example 6: Preparation of a Dusting Powder Containing Collagenase, Corn Starch Glycolate and Glidant (Formulation 5)

The collagenase, in lyophilic form, is measured so that it corresponds to an activity of 5 nkat/g of finished product.

| | |
|---|---|
| Collagenase | equivalent to 5 nkat/g |
| Colloidal silicon dioxide | 0.2 g |
| Corn starch glycolate | q.s. for 100 g |

About half the quantity of gelling polymer is weighed and introduced into the container; the collagenase is weighed and introduced into the container. Finally, the remaining quantity of gelling polymer and glidant is weighed and introduced into the container. The preparation is performed by direct mixing of the powders in a parallelepipedal polyethylene vial closed with a polyethylene sub-cap and a polypropylene screw cap, with a sufficient capacity to leave at least 40-50% of empty headspace. The vial, fixed in the arm of a V mixer in an oblique position (45 degrees), rotates obliquely around its minor axis at the speed of 50 rpm. Mixing proceeds until the mixture is homogenous.

Example 7: Preparation of a Dusting Powder Containing Collagenase, Corn Starch Glycolate and Glidant (Formulation 6)

The collagenase, in lyophilic form, is measured so that it corresponds to an activity of 5 nkat/g of finished product.

| | |
|---|---|
| Collagenase | equivalent to 5 nkat/g |
| Colloidal silicon dioxide | 1 g |
| Corn starch glycolate | q.s. for 100 g |

For preparation, see Example 5.

As stated, the pre- and post-sterilisation rheology of said dusting powders, and their performance in terms of collagenase release, were evaluated after hydration. This last test was conducted by comparison with a standard product (Bionect Start®) containing collagenase in a lipophilic carrier.

Pre- and Post-Sterilisation Rheological Evaluation

The samples tested were prepared according to Examples 1 and 3, which represent the most complex formulations of those identified.

1 g each of non-sterile Formulation 1 and Formulation 3 was hydrated with 7 ml of saline solution; the same procedure was performed on 1 g of the same formulations pre-sterilised with γ rays (dose 25 kGray). The gels thus obtained were analysed to evaluate viscous moduli G' and G" with a HAAKE mod. Mars II viscometer equipped with plate-cone measurement with 60 mm diameter and 1° angle; the measurement was performed at 20±0.5° C. under rotation control with a speed ramp with constant acceleration from 0 to 5 sec-1 in 8 minutes; the interpolation was performed at 1.0 sec-1. The results are illustrated in FIG. 11

(Pre- and post-sterilisation rheological evaluation): each formulation evidently retains its rheological properties practically unchanged, even after sterilisation. Formulation 1, without glidant, has slightly superior G' and G" moduli, but not to a statistically significant extent. This means that the glidant has no effect on the rheology, and whether it is used or not therefore depends on the operating conditions. However, it must be emphasised that the polymer selected retains the characteristics of adherence and viscosity identified in the preliminary tests, which are necessary for the optimum release of the enzyme contained in the formulation.

Evaluation of Collagenolytic Activity

These tests test the behaviour of the formulations with and without hyaluronic acid compared with a commercial reference product (Bionect Start®) containing collagenase in a lipophilic carrier (ointment) and hyaluronic acid.

As the glidant has no effect on the enzyme activity of collagenase, it was decided to test Formulations 1 (with HA) and 4 (without HA). The degradative activity of the enzyme is determined with a quantitative assay on a standard commercial substrate (Collagenase Chromophore substrate kit—Fluka 27669). The method was suitably modified to allow testing of the powdered formulation of the samples examined, and simulation of the conditions to which said preparations will be subjected after application in vivo. The assay is based on hydrolysis of the specific collagenase substrate: 4-phenylazobenzyloxycarbonyl-Pro-Leu-Gly-Pro-D-Arg-OH (component A). Said substrate is degraded to Pz-Pro-Leu-OH (yellow-orange fragment) and H-Gly-Pro-D-Arg-OH in the presence of the collagenase enzyme. The peptide Pz-Pro-Leu-OH is soluble in organic solvents, and is extracted with ethyl acetate from the mixture acidified with citric acid. The excess undegraded substrate remains in the acidified aqueous phase. Pz-Pro-Leu-OH in ethyl acetate is quantitatively determined spectrophotometrically by reading at 320 nm.

Materials and Methods
Collagenase Chromophore substrate kit—Fluka 27669
Formulation 1
Formulation 4
Bionect Start®
Saline solution
TRIS Buffer
25 mM citric acid
Ethyl acetate
anhydrous $Na_2SO_4$.
3 tests are performed for each formulation.
Step 1.

Figure 9:
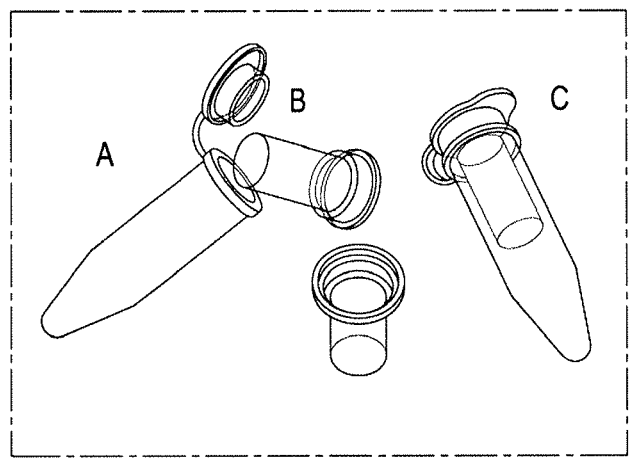
FIG. 9 is a photograph of a 1.5 ml Corning Costar SpinX tube (A), a container bearing a membrane with a porosity of 0.22 μm (B), and a tube with a substrate solution (C).

1.1 ml of substrate solution at the concentration of 2.6 mM is placed in a 1.5 ml Corning Costar SpinX tube (Sigma, FIG. 9A), as reported in the Fluka commercial assay method. 100 mg of each powdered collagenase formulation (Formulations 1 and 4), which is hydrated with 4 times its weight in saline solution, is inserted in the container bearing the membrane with a porosity of 0.22 μm (FIG. 9B). The container is hermetically sealed with a suitable cap to prevent the powder from swelling due to further absorption of liquid during the experiment. The container is housed in the tube with the substrate solution (FIG. 9C). The tube is hermetically sealed and inverted to allow contact between the substrate solution and the container membrane. The collagenase and the substrate can cross the membrane freely, whereas the powders are trapped in the container. The entire preparation is incubated at 32° C. The containers are replaced as specified in the protocol to simulate daily application, application every two days and a single application.

Figure 10:
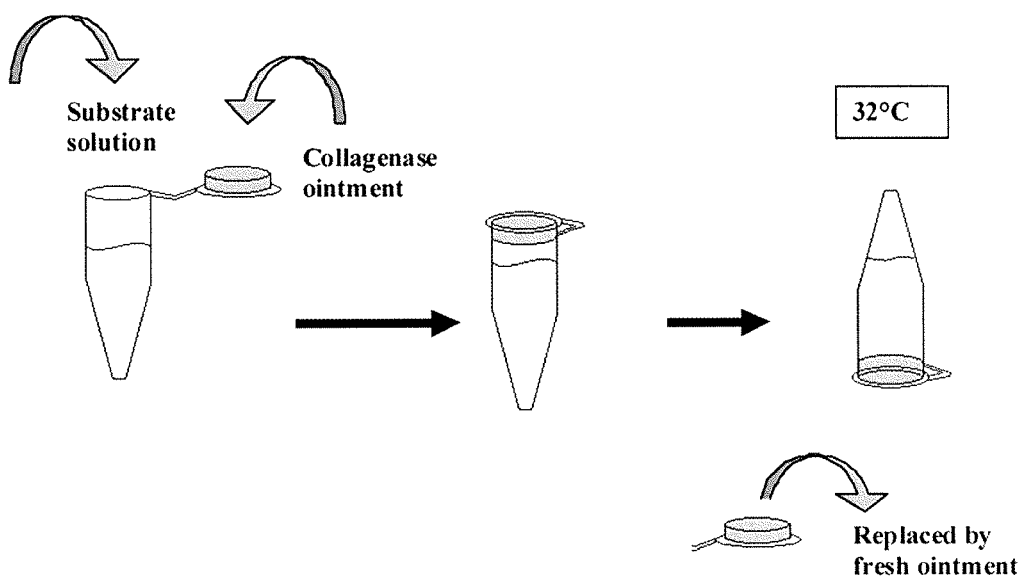
FIG. 10 illustrates the evaluation of collagenolytic activity in the present invention.

For Bionect Start®, which is an ointment, Step 1 is modified as described below:

0.6 ml of substrate solution at the concentration of 1.3 mM is placed in 1.5 ml Eppendorf tubes (FIG. 10: Eppendorf tube for modified step 1), as reported in the Fluka commercial assay method. The caps of the Eppendorf tubes are filled with approx. 250 mg of Bionect Start®, which is placed in contact with the substrate solution and incubated at 32° C. The caps are replaced as specified in the protocol to simulate daily application, application every two days and a single application.

Step 2:

When the pre-set contact period has elapsed, 125 μl of the substrate mixture, treated as described in Step 1, is taken up at each fixed time-point and placed in a 1.5 ml Eppendorf tube. 250 μl of citric acid (25 mM) and 1.25 ml of ethyl acetate are added to this solution. The solution is stirred for 15 seconds and centrifuged. The ethyl acetate, which contains the hydrolysed substrate, is transferred to an Eppendorf tube containing anhydrous $Na_2SO_4$. After agitation and centrifugation of the Eppendorf tube, the organic phase is transferred to a new Eppendorf tube. The hydrolysed substrate contained in the organic phase is determined spectrophotometrically at 320 nm.

The data analysis is reported in FIGS. 12-14.

It is immediately evident that powdered formulations perform far better than the reference product at each of the application frequencies tested, and for each time-point considered.

In particular, the values of Formulations 1 and 4 were always highly significant compared with the reference product, demonstrating their better efficacy, which means fewer applications for the patient. In any event it is obvious that powdered formulations work far better than those containing collagenase in a lipophilic carrier. This means not only that the collagenase present in the powdered formulations acts in the aqueous environment created when exudate is absorbed by corn starch glycolate, demonstrating the stability in aqueous solution previously claimed, but also that it operates surprisingly better than expected.

As regards the injectable formulations, as previously stated they substantially exploit the purity of the enzyme obtained by the process described above and its surprising stability in an aqueous carrier, both at ambient T and at temperatures ranging between −20 and −80° C. The injectable compositions preferably consist of collagenase in freeze-dried form reconstituted in aqueous solution, preferably at the time of use, and comprise, per unit dose:

collagenase obtained according to the process described, in a quantity equivalent to activity of between 120 and 450 nkat;

sterile saline solution (NaCl 0.9%);

optionally, HA with a weight average molecular weight of between 750 and 1200 kDa, in a concentration ranging between 1 and 30 mg/ml of saline solution, preferably between 8 and 20 mg/ml, and even more preferably between 10 and 15 mg/ml.

Some examples of preparation of injectable solutions of collagenase will now be described by way of example but not of limitation.

Example 8: Preparation of an Injectable Solution of Collagenase in Sterile Saline Solution (0.9% NaCl)

| | |
|---|---|
| Collagenase | equivalent to 196 nkat |
| Sterile saline solution | 1 ml |

The enzyme in lyophilic form, contained in a suitable sterile ampoule, is reconstituted with 0.35 ml of sterile saline solution, taken up with a graduated syringe. After gentle stirring a stable solution is obtained.

Example 9: Preparation of an Injectable Solution of Collagenase in Sterile Saline Solution (0.9% NaCl)

| | |
|---|---|
| Collagenase | equivalent to 392 nkat |
| Sterile saline solution | 1 ml |

The enzyme in lyophilic form, contained in a suitable sterile ampoule, is reconstituted with 0.7 ml of sterile saline solution, taken up with a graduated syringe. After gentle stirring a stable solution is obtained.

Example 10: Preparation of an Injectable Solution of Collagenase Formulated in 750 kDa MW HA

| | |
|---|---|
| Collagenase | equivalent to 196 nkat |
| HA solution | 1 ml |

The HA solution is preconstituted by dissolving 10 mg of pre-micronised HA contained in a suitable sterile ampoule in 1 ml of sterile saline solution. The enzyme in lyophilic form is reconstituted with 0.35 ml of HA solution, measured with a graduated syringe. After gentle stirring until the collagenase powder has dissolved, a stable solution is obtained.

Example 11: Preparation of an Injectable Solution of Collagenase Formulated in 1200 kDa MW HA

| | |
|---|---|
| Collagenase | equivalent to 392 nkat |
| HA solution | 1 ml |

The HA solution is preconstituted by dissolving 15 mg of pre-micronised HA contained in a suitable sterile ampoule in 1 ml of sterile saline solution. The enzyme in lyophilic form is reconstituted with 0.7 ml of HA solution, measured with a graduated syringe. After gentle stirring until the collagenase powder has dissolved, a stable solution is obtained.

The solutions thus obtained can be stored at 4° C., although it is preferable to inject them immediately after preparation or within 8 hours. In addition to the typically therapeutic uses described above, the collagenase according to the invention can also be used to dissociate tissues and isolate cell clusters or single cells, for both therapeutic and experimental research purposes. This application is used, for example, in the Langerhans islet cell transplantation procedure to isolate the islet cells from the surrounding pancreatic tissue. Collagenase can also be used successfully to isolate cardiomyocytes, hepatocytes and tumour cells for the purpose of the developing the corresponding vaccine, and in general for all cells usable in the tissue engineering field (bone, cartilage, thyroid, etc).

The invention claimed is:

1. A process for the production and purification of collagenase from *Vibrio alginolyticus* chemovar. *lophagus*, comprising the following stages:

Stage A: Inoculation of *Vibrio Alginolyticus* chemovar. *lophagus* into an Erlenmeyer flask and fermentation with culture broth of non-bovine animal origin;

Stage B: Clarification of the fermented broth thus obtained by tangential flow ultrafiltration with 100-500 kD Molecular Weight Cut-Off (MWCO) cassettes;

Stage C: Dialysis and concentration of the clarified medium obtained in stage B, by tangential flow ultrafiltration with 5-30 kD MWCO cassettes;

Stage D: Purification of the solution containing collagenase obtained in Stage C, by anion-exchange resin carrying weak basic groups, at a pH of between 6.9 and 7.4;

Stage E: Dialysis and concentration of the fractions with collagenolytic activity collected in Stage D, by tangential flow ultrafiltration with 10-50 kD MWCO cassettes;

Stage F: Purification of the solution thus obtained, by anion-exchange resin carrying strong basic groups, at a pH of between 6.9 and 7.4;

Stage G: Diafiltration and concentration of the fractions with collagenolytic activity ≥95% originating from stage F, by tangential flow ultrafiltration with 10-50 kD MWCO cassettes;

Stage H: Filtration of the solution containing collagenase thus obtained, through an 0.2 μm absolute filter, and storage at a temperature of between −20° and −80° C.;

wherein the thus obtained collagenase from *Vibrio alginolyticus* chemovar. *lophagus* being characterized by:

molecular weight 82 Kda;

specific activity between 1000 and 1800 nkat/mg;

purity between 98.0 and 100%;

no microbial or protein contaminants;

stability at a pH of between 5.5 and 11;

stability in aqueous solution at a temperature ranging between 4° and 40° C.;

stability in aqueous solution at 4° C. for 30 days;

stability in aqueous solution at a temperature ranging between −20° C. and −80° C. for 24-48 months;

lyophilisability to obtain a stable lyophilic powder; and caseinase activity is less than 1.0 U/ml.

2. The process according to claim 1, wherein the culture broth is of porcine animal origin or is a mixture of porcine and plant origin.

3. The process according to claim 1 or 2, wherein the anion-exchange resin carrying the weak basic groups carries diethylaminoalkyl groups and the anion-exchange resin carrying strong basic groups carries quaternary ammonium groups.

* * * * *